US008017394B2

(12) United States Patent
Adkisson, IV et al.

(10) Patent No.: US 8,017,394 B2
(45) Date of Patent: Sep. 13, 2011

(54) METHOD FOR CHONDROCYTE EXPANSION WITH PHENOTYPE RETENTION

(75) Inventors: Huston Davis Adkisson, IV, St. Louis, MO (US); Curt L Milliman, St. Louis, MO (US); Neil Kizer, Crestwood, MO (US)

(73) Assignee: ISTO Technologies, Inc., St. Louis, MO (US)

( * ) Notice: Subject to any disclaimer, the term of this patent is extended or adjusted under 35 U.S.C. 154(b) by 866 days.

(21) Appl. No.: 11/859,524

(22) Filed: Sep. 21, 2007

(65) Prior Publication Data
US 2008/0081369 A1 Apr. 3, 2008

Related U.S. Application Data

(63) Continuation-in-part of application No. 10/956,971, filed on Oct. 1, 2004, now Pat. No. 7,273,756.

(51) Int. Cl.
*C12N 5/00* (2006.01)
(52) U.S. Cl. .......................... 435/377; 435/325; 435/375
(58) Field of Classification Search ........................ None
See application file for complete search history.

(56) References Cited

U.S. PATENT DOCUMENTS

| | | | |
|---|---|---|---|
| 4,356,261 A | 10/1982 | Kuettner | |
| 5,658,582 A | 8/1997 | Dorigatti et al. | |
| 5,676,964 A | 10/1997 | Della Valle et al. | |
| 5,716,404 A | 2/1998 | Vacanti et al. | |
| 5,723,331 A * | 3/1998 | Tubo et al. ................ | 435/366 |
| 5,753,485 A | 5/1998 | Dwulet et al. | |
| 5,830,741 A | 11/1998 | Dwulet et al. | |
| 6,150,163 A * | 11/2000 | McPherson et al. .......... | 435/384 |
| 6,197,061 B1 * | 3/2001 | Masuda et al. .............. | 623/11.11 |
| 6,235,316 B1 | 5/2001 | Adkisson | |
| 6,251,876 B1 | 6/2001 | Bellini et al. | |
| 6,582,960 B1 | 6/2003 | Martin et al. | |
| 6,617,161 B2 | 9/2003 | Luyten et al. | |
| 6,645,764 B1 | 11/2003 | Adkisson | |
| 6,699,471 B2 | 3/2004 | Radice et al. | |
| 7,074,615 B2 | 7/2006 | Chaney et al. | |
| 2003/0077821 A1 | 4/2003 | Sah et al. | |
| 2003/0215426 A1 | 11/2003 | French et al. | |
| 2006/0073588 A1 | 4/2006 | Adkisson et al. | |

FOREIGN PATENT DOCUMENTS
WO 2007092801 A2 8/2007

OTHER PUBLICATIONS

ISR dated Dec. 11, 2008 regarding PCT/US2008/77161, four (4) pages.
Adkisson et al., "In Vitro Generation of Scaffold Independent Neocartilage," Clin. Orthopaedics and Related Res., 2001, pp. S280-S294, vol. 391S.
Barbero et al., "Age related Changes in Human Articular Chondrocyte Yield, Proliferation and Post-Expansion Chondrogenic Capacity," Osteocartilage Cartilage 12: 476-484, 2004.
Benya et al., "Dedifferentiated Chondrocytes Reexpress the Differentiated Collagen Phenotype When Cultured in Agarose Gels," Cell, 1982, pp. 215-224, vol. 30.
Cima et al., "Hepatocyte Culture on Biodegradable Polymeric Substrates," Biotechnology and Bioengineering, 1991, pp. 145-158, vol. 38.
Crosslinkers product literature, 2004, Rockford, Illinois, pp. 429-440.
De Bari et al., "Failure of In Vitro-Differentiated Mesenchymal Stem Cells from the Synovial Membrane to Form Ectopic Stable Cartilage in Vivo," Arthritis & Rheumatism, 2004, pp. 142-150, vol. 50.
De Bari et al., "Human Periosteum-Derived Cells Maintain Phenotypic Stability and Chondrogenic Potential Throughout Expansion Regardless of Donor Age," Arthritis & Rheumatism, 2001, pp. 85-95, vol. 44.
Dell'Accio et al., "Molecular Markers Predictive of the Capacity of Expanded Human Articular Chondrocytes to Form Stable Cartilage in Vivo," Arthritis & Rheumatism, 2001, pp. 1608-1619, vol. 44.
Farndale et al., "Improved Quantitation and Discrimination of Sulphated Glycosaminoglycans by Use of Dimethylmethylene Blue," Biochimica et Biophysica Acta, 1986, pp. 173-177, vol. 883.
Häuselmann et al., "Phenotypic Stability of Bovine Articular Chondrocytes After Long-Term Culture in Alginate Beads," J. Cell Sci.,I 1994, pp. 17-27, vol. 107.
Häuselmann et al., "Adult Human Chondrocytes Cultured in Alginate Form a Matrix Similar to Native Human Articular Cartilage," Am. J. Physiol., 1996, pp. C742-C752, vol. 271.
Hermanson, Bioconjugate Techniques, "Modification with Synthetic Polymers," 1996, San Diego, Academic Press, Inc., Ch. 15, p. 622.
Homicz et al., "Effects of Serial Expansion of Septal Chondrocytes on Tissue-Engineered Neocartilage Composition," Otolaryngol. Head Neck Surg., 2002, pp. 398-408, vol. 127.
Huang et al., "Chondrogenic Potential of Multipotential Cells from Human Adipose Tissue," Plast. Reconstr. Surg., 2004, pp. 585-594, vol. 113.
Hunziker, "Articular Cartilage Repair: Basic Science and Clinical Progress. A Review of the Current Status and Prospects," Osteoarthritis and Cartilage, 2001, pp. 432-463, vol. 10.
Jakob et al., "Specific Growth Factors During the Expansion and Redifferentiation of Adult Human Articular Chondrocytes Enhance Chondrogenesis and Cartilaginous Tissue Formation in Vitro," J. Cell. Biochem., 2001, pp. 368-377, vol. 81.
Kavalkovich et al., "Chondrogenic Differentiation of Human Mesenchymal Stem Cells Within an Alginate Layer Culture System," In Vitro Cell Dev. Biol.—Animal, 2002, pp. 457-466, vol. 38.

(Continued)

*Primary Examiner* — Lora E Barnhart
(74) *Attorney, Agent, or Firm* — Polsinelli, Shughart, PC

(57) ABSTRACT

The present invention provides a method for expanding a population of chondrocytes that maintains chondrocyte phenotype during the expansion by culturing the population in a defined serum-free expansion medium containing one or more cytokines and under low attachment conditions. The method further solves diffusion problems during the subsequent stage of extracellular matrix production by use of a perforated polycarbonate substrate that results in a randomly organized cultured neocartilage tissue. Chondrocytes expanded and cultured in this manner can be used in various medical applications to repair cartilaginous tissues that have been injured by trauma or disease.

15 Claims, 13 Drawing Sheets

OTHER PUBLICATIONS

Kogler et al., "A New Human Somatic Stem Cell Form Placental Cord Blood with Intrinisic Pluripotent Differentiation Potential," J. Exp. Med., 2004, pp. 123-135, vol. 200.

Kujawa et al., "Hyaluronic Acid Bonded to Cell Culture Surfaces Inhibits the Program of Myogenesis," Developmental Biol., 1986, pp. 10-16, vol. 113.

Kujawa et al., "Substrate-Bonded Hyaluronic Acid Exhibits a Size-Dependent Stimulation of Chondrogenic Differentiation of Stage 24 Limb Mesenchymal Cells in Cultures," Developmental Biol., 1986, pp. 519-528, vol. 114.

Kujawa et al., "Hyaluronic Acid Bonded to Cell-Culture Surfaces Stimulates Chondrogenesis in Stage 24 Limb Mesenchyme Cell Cultures," Developmental Biol., 1986, pp. 504-518, vol. 114.

Laurent et al., "Hyaluronan,"FASEB J., 1992, pp. 2397-2404, vol. 6.

Laurent et al., "Structure of Hyaluronic Acid," Chemistry and Molecular Biology of the Intercellular Matrix, 1970, (Balazs ed., Academic Press, New York), pp. 703-732, vol. 2.

Liu et al., "An Osteoconductive Collagen/Hyaluronate Matrix for Bone Regeneration," Biomaterials, 1999, pp. 1097-1108, vol. 20.

Mackay et al., "Chondrogenic Differentiation of Cultured Human Mesenchymal Stem Cells from Marrow," Tissue Engineering, 1998, pp. 415-428, vol. 4.

Malpeli et al., "Serum-Free Growth Medium Sustains Commitment of Human Articular Chondrocyte Through Maintenance of Sox9 Expression," Tissue Engineering, 2004, pp. 145-155, vol. 10.

Mandl et al., "Serum-Free Medium Supplemented with High-Concentration FGF2 for Cell Expansion Culture of Human Ear Chondrocytes Promotes Redifferentiation Capacity," Tissue Engineering, 2002, pp. 573-580, vol. 8.

Mandl et al., "Multiplication of Human Chondrocytes with Low Seeding Densities Accelerates Cell Yield Without Losing Redifferentiation Capacity," Tissue Engineering, 2004, pp. 109-118, vol. 10.

Ornitz et al., "Fibroblast Growth Factors," Genome Biol., 2001, pp. 1-12, vol. 2.

Ornitz, "FGFs, Heparan Sulfate and FGFRs: Complex Interactions Essential for Development," BioEssays, 2000, pp. 108-112, vol. 22.

Osman et al., "Combined Transgenic Expression of a $\alpha$-Galactosidase and $\alpha$1, 2-Fucosyltransferase Leads to Optimal Reduction in the Major Xenoepitope Gal$\alpha$ (1,3)Gal," Proc. Natl. Acad. Sci. USA, 1997, pp. 14677-14682, vol. 94.

Plotnikov et al., "Crystal Structures of Two FGF-FGFR Complexes Reveal the Determinants of Ligand-Receptor Specificity," Cell, 2000, pp. 413-424, vol. 101.

Reginato et al., "Formation of Nodular Structures Resembling Mature Articular Cartilage in Long-Term Primary Cultures of Human Fetal Epiphyseal Chondrocytes on a Hydrogel Substrate," Arthritis & Rheumatism, 1994, pp. 1338-1349, vol. 37.

Sandrin et al., "Enzymatic Remodelling of the Carbohydraqte Surface of a Xenogenic Cell Substantially Reduces Human Antibody Binding and Complement-Mediated Cytolysis," Nature Medicine, 1995, pp. 1261-1267, vol. 1.

Sekiya et al., "Dexamethasone Enhances SOX9 Expression in Chondrocytes," J. Endocrinol., 2001, pp. 573-579, vol. 169.

Singley et al., "The Spatial Distribution of Hyaluronic Acid and Mesenchymal Condensation in the Embryonic Chick Wing," Dev. Biol., 1981, pp. 102-120, vol. 84.

Stegemann et al., "Determination of Hydroxyproline," Clinica Chemica Acta, 1967, pp. 267-273, vol. 18.

Turley et al., "Spontaneous Glycosylation of Glycosaminoglycan Substrates by Adherent Fibroblasts," Cell, 1979, pp. 109-115, vol. 17.

Vacanti et al., "Beyond Transplantation— Third Annual Samuel Jason Mixter Lecture," Arch. Surg., 1988, pp. 545-549, vol. 123.

Vacanti et al., "Selective Cell Transplantation Using Bioabsorbable Artifical Polymers as Matrices," J. Pediatric Surg., 1988, pp. 3-9, vol. 23.

West et al., "Angiogenesis Induced by Degradation Products of Hyaluronic Acid," Science, 1985, pp. 1324-1326, vol. 228.

Yoon et al., "Maintenance of Differentiated Phenotype of Articular Chondrocytes by Protein C and Extracellular Signal-Regulated Protein Kinase," J. Biol. Chem., 2002, pp. 8412-8420, vol. 277.

Aigner et al., "Cartilage Tissue Engineering with Novel Nonwoven Structured Biomaterial Based on Hyaluronic Acid," J. Biomed. Mater. Res., 1998, pp. 172-181, vol. 42.

Bradham et al., "In Vivo Cartilage Formation From Growth Factor Modulated Articular Chondrocytes," Clin. Ortho. Rel. Res., 1998, pp. 239-249, vol. 352.

Ehlers et al., "Effects of Hyaluronic Acid on the Morphology and Proliferation of Human Chondrocytes in Primary Cel Culture," Annals Anat., 2001, pp. 13-17, vol. 183.

Hegewald et al., Hyaluronic Acid and Autologous Synovial Fluid Induce Chondrogenic Differentiation . . . Tissue and Cell, 2004, pp. 431-438, vol. 36.

Crabb et al., "Synergistic Effect of Transforming Growth Factor $\beta$ and Fibroblast Growth Factor on DNA Synthesis in Chick Growth Plate Chondrocytes," Journal of Bone and Mineral Research, 1990, pp. 1105-1112, vol. 5, No. 11.

Morales, "Transforming Growth Factor-$\beta$ and Insulin-like Growth Factor-1 Restore Proteoglycan Metabolism of Bovine Articular Cartilage after Depletion by Retinoic Acid," Archives of Biochemistry and Biophysics, 1994, pp. 190-198, vol. 315. No. 1.

Solursh et al., "Depression by Hyaluronic Acid of Glycosaminoglycan Synthesis by Cultured Chick Embryo Chondrocytes," Developmental Biology, 1974, pp. 233-244, vol. 41.

* cited by examiner

SEQUENCE LISTING

```
<160> NUMBER OF SEQ ID NOS: 22

<210> SEQ ID NO 1
<211> LENGTH: 23
<212> TYPE: DNA
<213> ORGANISM: Artificial
<220> FEATURE:
<223> OTHER INFORMATION: AGC1-2S primer, Aggrecan core

<400> SEQUENCE: 1
gaaacttcag accatgacaa ctc                                           23
```

```
<210> SEQ ID NO 2
<211> LENGTH: 21
<212> TYPE: DNA
<213> ORGANISM: Artificial
<220> FEATURE:
<223> OTHER INFORMATION: AGC1-2AS primer, Aggrecan core

<400> SEQUENCE: 2
accagcagca ctacctcctt c                                              21

<210> SEQ ID NO 3
<211> LENGTH: 20
<212> TYPE: DNA
<213> ORGANISM: Artificial
<220> FEATURE:
<223> OTHER INFORMATION: B7-H1-1S primer, B7-H1

<400> SEQUENCE: 3
gctcttggtg ctggctggtc                                                20

<210> SEQ ID NO 4
<211> LENGTH: 23
<212> TYPE: DNA
<213> ORGANISM: Artificial
<220> FEATURE:
<223> OTHER INFORMATION: B7-H1-1AS primer, B7-H1

<400> SEQUENCE: 4
tcagatatac taggtgtagg gaa                                            23

<210> SEQ ID NO 5
<211> LENGTH: 24
<212> TYPE: DNA
<213> ORGANISM: Artificial
<220> FEATURE:
<223> OTHER INFORMATION: B7-1-6S primer, B7-1

<400> SEQUENCE: 5
gccatcaaca caacagtttc ccaa                                           24

<210> SEQ ID NO 6
<211> LENGTH: 25
<212> TYPE: DNA
<213> ORGANISM: Artificial
<220> FEATURE:
<223> OTHER INFORMATION: B7-1-6AS primer, B7-1 (CD80)

<400> SEQUENCE: 6
cagggcgtac actttccctt ctcaa                                          25

<210> SEQ ID NO 7
<211> LENGTH: 23
<212> TYPE: DNA
<213> ORGANISM: Artificial
<220> FEATURE:
<223> OTHER INFORMATION: B7-2-6S primer, B7-2

<400> SEQUENCE: 7
ctctctggtg ctgctcctct gaa                                            23

<210> SEQ ID NO 8
<211> LENGTH: 27
<212> TYPE: DNA
<213> ORGANISM: Artificial
<220> FEATURE:
<223> OTHER INFORMATION: B7-2-6AS primer, B7-2 (CD86)

<400> SEQUENCE: 8
```

```
ctgtgggctt tttgtgatgg atgatac                                          27
```

<210> SEQ ID NO 9
<211> LENGTH: 20
<212> TYPE: DNA
<213> ORGANISM: Artificial
<220> FEATURE:
<223> OTHER INFORMATION: Col1A1-3S primer, Col1A1

<400> SEQUENCE: 9

```
cgagggccaa gacgaagaca                                                  20
```

<210> SEQ ID NO 10
<211> LENGTH: 22
<212> TYPE: DNA
<213> ORGANISM: Artificial
<220> FEATURE:
<223> OTHER INFORMATION: Col1A1-3AS primer, Col1A1

<400> SEQUENCE: 10

```
cttggtcggt gggtgactct ga                                               22
```

<210> SEQ ID NO 11
<211> LENGTH: 26
<212> TYPE: DNA
<213> ORGANISM: Artificial
<220> FEATURE:
<223> OTHER INFORMATION: Col2A1-8S primer, Col2A1

<400> SEQUENCE: 11

```
caccctgagt ggaagagtgg agctac                                           26
```

<210> SEQ ID NO 12
<211> LENGTH: 23
<212> TYPE: DNA
<213> ORGANISM: Artificial
<220> FEATURE:
<223> OTHER INFORMATION: Col2A1-8AS primer, Col2A1

<400> SEQUENCE: 12

```
cagtgttggg agccagattg tca                                              23
```

<210> SEQ ID NO 13
<211> LENGTH: 27
<212> TYPE: DNA
<213> ORGANISM: Artificial
<220> FEATURE:
<223> OTHER INFORMATION: Col9A1-5S primer, Col9A1

<400> SEQUENCE: 13

```
aagcacaact cagtgcccca acaaaac                                          27
```

<210> SEQ ID NO 14
<211> LENGTH: 20
<212> TYPE: DNA
<213> ORGANISM: Artificial
<220> FEATURE:
<223> OTHER INFORMATION: Col9A1-6AS primer, Col9A1

<400> SEQUENCE: 14

```
atcccatcac ggccatcaca                                                  20
```

<210> SEQ ID NO 15
<211> LENGTH: 27
<212> TYPE: DNA
<213> ORGANISM: Artificial

```
<220> FEATURE:
<223> OTHER INFORMATION: Col11A1-2S primer, Col11A1

<400> SEQUENCE: 15
aagcacaact cagtgcccca acaaaac                                          27

<210> SEQ ID NO 16
<211> LENGTH: 24
<212> TYPE: DNA
<213> ORGANISM: Artificial
<220> FEATURE:
<223> OTHER INFORMATION: Col11A1-2AS primer, Col11A1

<400> SEQUENCE: 16
ctacccgatg ccacttcccg tcag                                             24

<210> SEQ ID NO 17
<211> LENGTH: 21
<212> TYPE: DNA
<213> ORGANISM: Artificial
<220> FEATURE:
<223> OTHER INFORMATION: GAPDH-1S primer, GAPDH

<400> SEQUENCE: 17
gcaaattcca tggcaccgtc a                                                21

<210> SEQ ID NO 18
<211> LENGTH: 20
<212> TYPE: DNA
<213> ORGANISM: Artificial
<220> FEATURE:
<223> OTHER INFORMATION: GAPDH-1AS primer, GAPDH

<400> SEQUENCE: 18 cagggtgct aagcagttgg                                                   20

<210> SEQ ID NO 19
<211> LENGTH: 26
<212> TYPE: DNA
<213> ORGANISM: Artificial
<220> FEATURE:
<223> OTHER INFORMATION: NCAD-1S primer, N-cadherin

<400> SEQUENCE: 19
ggaaaagtgg caagtggcag taaaat                                           26

<210> SEQ ID NO 20
<211> LENGTH: 26
<212> TYPE: DNA
<213> ORGANISM: Artificial
<220> FEATURE:
<223> OTHER INFORMATION: NCAD-1AS primer, N-cadherin

<400> SEQUENCE: 20
ccgagatggg gttgataatg aagata                                           26

<210> SEQ ID NO 21
<211> LENGTH: 23
<212> TYPE: DNA
<213> ORGANISM: Artificial
<220> FEATURE:
<223> OTHER INFORMATION: SOX9-1S primer, SOX-9

<400> SEQUENCE: 21
gtcaacggct ccagcaagaa caa                                              23
```

-continued

```
<210> SEQ ID NO 22
<211> LENGTH: 19
<212> TYPE: DNA
<213> ORGANISM: Artificial
<220> FEATURE:
<223> OTHER INFORMATION: SOX9-1AS primer, SOX-9

<400> SEQUENCE: 22
gctccgcctc ctccacgaa                                                  19
```

METHOD FOR CHONDROCYTE EXPANSION WITH PHENOTYPE RETENTION

CROSS-REFERENCE TO RELATED APPLICATION

This application is a continuation-in-part application of U.S. patent application Ser. No. 10/956,971 filed Oct. 1, 2004, which is incorporated herein by reference in its entirety.

STATEMENT REGARDING FEDERALLY SPONSORED RESEARCH OR DEVELOPMENT

Research relating to the invention was supported in part by a NIST sponsored ATP Award 70NANB1H3027. The Government has certain rights to paid up, royalty-free non-exclusive license of the invention.

REFERENCE TO A SEQUENCE LISTING

The Sequence Listing, which is a part of the present disclosure, includes a computer file "10500-0063_ST25.txt" generated by U.S. Patent & Trademark Office Patent In Version 3.4 software comprising nucleotide and/or amino acid sequences of the present invention. The subject matter of the Sequence Listing is incorporated herein by reference in its entirety.

BACKGROUND OF THE INVENTION

Millions of people in the United States alone are afflicted with painful inflammatory or degenerative arthritis which limits normal joint function and results in loss of quality of life. The primary cause of degenerative arthritis is breakdown of the cartilage matrix. Cartilage is a smooth, flexible connective tissue covering the ends of a joint which functions to cushion the bone and allow the joint to move easily without pain. Loss of joint articular cartilage due to traumatic injury or disease ultimately results in joint stiffening caused by "bone on bone movement" and painful exposure of nerve endings in subchondral bone.

In mammals, cartilage contributes to the structure of several organs and systems like the articular surface of joints and other joint-associated structures, including the ear, the nose, the larynx, the trachea, the bronchi, structures of the heart valves, etc. There are different types of cartilage in mammals: fibro-cartilage, elastic cartilage and hyaline cartilage. Fibro-cartilage contains an abundance of type I collagen and is found in the intervertebral disks and ligaments. Elastic cartilage contains elastin fibrils and is found in the pinna of the ear and in the epiglottis. Hyaline cartilage, a semi-transparent and clear cartilage tissue found in the cartilagenous walls of the trachea and bronchia, the costal cartilage and growth plate, as well as in cartilage of the nose, larynx and diarthroidal joints, contains neither type I collagen nor elastin. Hyaline cartilage having a distinctive combination of cartilage-specific collagens (types II, VI, IX, and XI) and aggregating proteoglycans (aggrecan) that give it the unique ability to withstand compressive forces is called articular cartilage.

Damage to articular cartilage results in lesions of the joint surface, and progressive degeneration of these lesions often leads to symptomatic joint pain, disability and reduced or disturbed functionality. Joint surface defects can be the result of various aetiologies, including inflammatory processes, neoplasias, post-traumatic and degenerative events, etc. Adult articular cartilage has a major shortcoming: unlike most tissues, it cannot repair itself. Lack of a blood supply in large part restricts the tissue's ability to recruit chondroprogenitor cells that can act to repair articular cartilage defects. Consequently, articular cartilage defects that have progressed to advanced degenerative disease require total joint arthroplasty to eliminate pain and to restore normal joint function.

Tissue-engineered growth of articular cartilage represents a biologic solution which may delay or reduce the need for metal- and polymer-based materials currently used in total joint arthroplasty. Several biologic approaches have attempted to repair or regenerate articular cartilage that is damaged by trauma or disease (Hunziker, 2003). The majority of these approaches combine cell-based therapy with biodegradable polymers to create a three-dimensional construct that can be transplanted into the knee. However, these experimental therapies have not produced long-lasting repair of hyaline cartilage (Buckwatler et al., 1990; Hunziker, 2002).

One technique that has gained FDA approval for cartilage repair is Autologous Chondrocyte Implantation (Carticel, Genzyme Surgery). In this procedure, a small tissue biopsy obtained from the patient's joint articular cartilage is taken to the lab where chondrocytes (cartilage cells) are isolated and expanded ex vivo for subsequent re-implantation into the patient in a second surgical procedure. A key limitation of this method is the relatively small number of donor cells that can be obtained at biopsy, and chondrocytes derived from adult articular cartilage appear to have a limited ability to produce cartilage matrix after expansion.

A successful tissue engineered approach to cartilage repair must make use of cells that can be expanded in a scalable process that is both efficient and reproducible and which retains the ability of the expanded chondrocytes to synthesize functional cartilage for use in transplantation. Currently, the most widely used technique for chondrocyte expansion is monolayer culture (U.S. Pat. No. 4,356,261). However, chondrocytes grown in monolayer culture using serum-containing medium undergo a process of dedifferentiation in which chondrocytes lose their spherical shape and acquire an elongated fibroblastic morphology. Biochemical changes associated with loss of native chondrocyte shape include arrested synthesis of cartilage-specific collagens and proteoglycans, subsequent initiation of type I and III collagen synthesis and increased synthesis of small non-aggregating proteoglycans.

Loss of chondrocyte phenotype during serial expansion in vitro poses a key limitation to the commercialization of orthobiologic approaches to articular cartilage repair. To counter dedifferentiation, chondrocytes traditionally have been suspended in three-dimensional environments such as hydrogels, e.g., agarose (Benya and Shafer, 1982) or alginate (Hauselmann et al., 1994 and 1996), pellet culture (Mackay et al., 1998; Jakob et al., 2001; Barbero et al., 2004), or three-dimensional scaffolds (Vacanti et al., 1998). Chondrocytes are reported to better retain their native rounded morphologic appearance and to synthesize macromolecules characteristic of hyaline cartilage when maintained in three-dimensional suspension culture after expansion. However, many of such cultured chondrocytes still produce type I collagen and small proteoglycans, indicating an "incompletely" restored cartilage phenotype. Furthermore, the potential for carry over of residual materials derived from the three-dimensional hydrogels can complicate the regulatory path. Alginate, for example, is reported to induce inflammation and may be cytotoxic when used in vivo. A logical approach to retain chondrocyte phenotype during in vitro expansion would be to recapitulate the in vivo microenvironment to which chondrocytes are naturally exposed during embryonic development. Therefore, matrices such as hyaluronic acid, type II and VI collagen or aggregating proteoglycans may serve as excellent substrates for chondrocyte expansion and growth, particularly in the absence of serum-derived factors. During embryonic development, condensation and proliferation of mesenchymal progenitor cells forms the cartilage anlagen through a process known as chondrogenesis. Further differentiation of the cartilage template results in formation of joint articular cartilage and bone. Many factors are believed to play a critical role in chondrogenesis, including the extracellular matrix, growth and differentiation factors, their antagonists as well as specific cell surface membrane receptors, including, N-cadherin, bone morphogenetic protein receptor type 1A (BMPR-1A) and bone morphogenetic protein receptor type 1B (BMPR-1B). An important component of the extracellular matrix, hyaluronic acid (HA) plays a critical role in cartilage development and in the maintenance of tissue homeostasis. HA is a non-sulfated, linear glycosaminoglycan of the extracellular matrix consisting of repeating units of ($\beta$, 1-4) D-glucuronic acid-($\beta$1-3)-N-acetyl-D-glucosamine (Laurent, 1970). HA is ubiquitously distributed in body tissues and has been shown to play an important role in a number of biological processes including embryonic development, wound healing and tumor growth by providing a provisional matrix that supports cellular migration, adherence, proliferation and differentiation (Laurent and Fraser, 1992). In its native state, HA exists as a high molecular weight polymer, usually in excess of $1 \times 10^6$ daltons. However, during morphogenesis, inflammation and tissue repair reduced molecular weight forms are generated by proteolytic cleavage. Hyaluronic acid of intermediate molecular weight (200,000 to 400,000) is reported to promote differentiation of chondrogenic progenitor cells (Kujawa et al., 1986 A and 1986B), whereas HA of reduced MW promotes angiogenesis (West et al., 1985). Such findings have led to the commercial development of HA-based scaffolds for tissue engineered growth of cartilage and bone, as a means of regenerating tissues that have been destroyed by trauma or disease (Campoccia et al., 1998 U.S. Pat. Nos. 6,251,876; 5,676,964; 5,658,582).

SUMMARY OF THE INVENTION

In one aspect the present invention provides a method for producing cartilage tissue in vitro, the method including isolating a population of chondrocytes from donor tissue, and expanding the population of chondrocytes in an expansion medium and on a substrate under low attachment conditions so that after at least 3.8 doublings of the chondrocyte population, at least 50% of the chondrocytes retain rounded morphology and hyaline cartilage gene expression. Expanding the population of cells under low attachment conditions includes expanding the population of cells using conditions established by using one of the following: an HA-modified substrate, a substrate having a coating of a low attachment material, or an unmodified substrate using an expansion medium comprising a low attachment agent in solution. The low attachment agent is, for example, hyaluronic acid (HA). In one embodiment, the expansion medium is serum-free medium, which optionally includes an amount of TGF-$\beta$. In an illustrative embodiment the expansion medium contains 10 ng/ml TGF-$\beta$. In another embodiment the expansion medium further includes FGF, and in an illustrative embodiment includes 100 ng/ml FGF by optionally includes up to 200 ng/ml FGF. In another embodiment the expansion medium further comprises L-Glutamine and Vitamin C. In another embodiment the method further includes injecting the expanded population of chondrocytes into a subject in need of cartilage repair. In another embodiment the method further includes, to produce extracellular matrix, seeding the population of chondrocytes in a tissue production medium on a polycarbonate substrate having a plurality of pores therethrough, the pores having an inner diameter of at least about 1 micron to about 12 microns, thereby producing a cultured cartilage tissue characterized by a random organization of cells.

In another aspect, the present invention provides a method for producing cartilage tissue in vitro, including isolating a population of chondrocytes from donor tissue, expanding the population of chondrocytes in an expansion medium, and seeding the population of chondrocytes in a tissue production medium on a polycarbonate substrate to produce extracellular matrix, the substrate having a plurality of pores therethrough, the pores having an inner diameter of at least 1 micron to about 12 microns, thereby producing a cultured cartilage tissue characterized by a random organization of cells. In one embodiment of the method, after at least 3.8 doublings of the chondrocyte population, at least 50% of the chondrocytes retain rounded morphology and hyaline cartilage gene expression. In another embodiment of the method, expanding the population of chondrocytes comprises providing low cell attachment conditions during expansion. In one embodiment, the expansion medium is a serum-free medium which in an exemplary embodiment includes TGF-$\beta$. The population of chondrocytes comprises, for example, synovial capsule chondrocytes, periosteum chondrocytes, juvenile or adult articular chondrocytes. In one embodiment the tissue production medium includes TGF-$\beta$, for example at in an amount of 10 ng/ml of the medium. In one embodiment expanding the population of chondrocytes includes a primary cell expansion and a secondary cell expansion that are optionally separated by a period of cryopreservation. In one embodiment, after seeding the population of chondrocytes on a polycarbonate substrate to produce extracellular matrix, the method further includes exposing the population of chondrocytes to TGF-$\beta$ in the tissue production medium for a period of about seven (7) days. In another embodiment, the method further includes maintaining the population of chondrocytes for a culture period of about forty-five (45) to about sixty-five (65) days in the tissue production medium. Maintaining the population of chondrocytes in a tissue production medium includes, for example, maintaining the population of chondrocytes at a predetermined level of oxygen and carbon dioxide in the tissue production medium.

In another aspect the present invention provides tissue culture apparatus including a polycarbonate substrate having multiple pores therethrough, the pores characterized by an inner diameter of at least about 1 micron to about 12 microns. In an exemplary embodiment, the tissue culture apparatus is a perforated polycarbonate membrane. In one embodiment the perforated polycarbonate membrane has a thickness of about 10 microns. In another embodiment, the pores in the perforated polycarbonate membrane are characterized by inner diameters distributed around 3 microns. In another embodiment, the tissue culture apparatus further includes side walls forming a perimeter around the polycarbonate substrate, the perimeter of a predetermined shape selected as a shape for a cultured tissue. The side walls are fabricated, for example, from a biocompatible polymer, which in one embodiment is semipermeable, and in another embodiment is impermeable. The biocompatible polymer can be, for example, polystyrene.

In another aspect the present invention provides a tissue culture insert including a polycarbonate substrate having a plurality of pores therethrough, the pores each having an inner diameter of at least about 1 micron to about 12 microns, and side walls forming a perimeter around the polycarbonate substrate, the perimeter of a predetermined shape selected as a shape for the cultured tissue.

In another aspect the present invention provides a cell culture including an expanded population of chondrocytes expressing a native phenotype and native level of hyaline cartilage gene expression, and a polycarbonate membrane having a plurality of pores therethrough, the pores having an inner diameter of at least about 1 micron to about 12 microns. The chondrocytes are, for example, human chondrocytes, and can be synovial capsule chondrocytes or periosteum chondrocytes, juvenile or adult articular chondrocytes, or transgenic chondrocytes resistant to immune-mediated xenograft rejection.

BRIEF DESCRIPTION OF THE DRAWINGS

FIG. 5, in two parts, FIG. 5A shows the morphologic appearance of chondrocytes after 10 day expansion culture on HA modified polystyrene using a defined serum-free medium containing variant fibroblast growth factor 2 (vFGF2), TGFβ and vitamin C. FIG. 5B shows the morphologic appearance of the same chondrocytes grown on unmodified polystyrene using the conditions identified in A.

FIGS. 8A and 8B, represent gene expression profile analyses obtained for freshly dissociated unpassaged cells (P0) and passage two cells (P2) chondrocytes harvested from a 14 month-old donor. Semi quantitative gene expression analysis was performed using the reverse transcriptase-polymerase chain reaction (RT-PCR). MW, molecular weight markers; GAP, glyceraldehydes-3-phosphate dehydrogenase; AGG, aggrecan core protein; COL 1A1, collagen type 1; COL 2A1, collagen type IIA; COL 9A1, collagen type IX; COL 11A1, collagen type XI; SOX9, cartilage specific transcription factor.

FIGS. 9A and 9B represent gene expression profile analyses obtained for articular chondrocytes derived from young donor cartilage that were expanded using methods of the described invention (Panel A) through 3.8 population doublings or in HL-1 Complete Serum-free Medium containing 10% serum and ascorbate (50 μg/mL) (Panel B) through 4.2 population doublings. NCAD, N-cadherin.

FIGS. 10A, 10B and 10C are photomicrographs of chondrocytes in expansion culture each using one of three different low attachment conditions, respectively: HA-modified polystyrene substrate (FIG. 10A), HA-supplemented chemically defined expansion medium on unmodified polystyrene substrate (FIG. 10B), and Ultra-Low Attachment polystyrene substrate material manufactured by Corning (FIG. 10C).

DETAILED DESCRIPTION OF THE PREFERRED EMBODIMENTS

Abbreviations and Definitions

Figure 1:
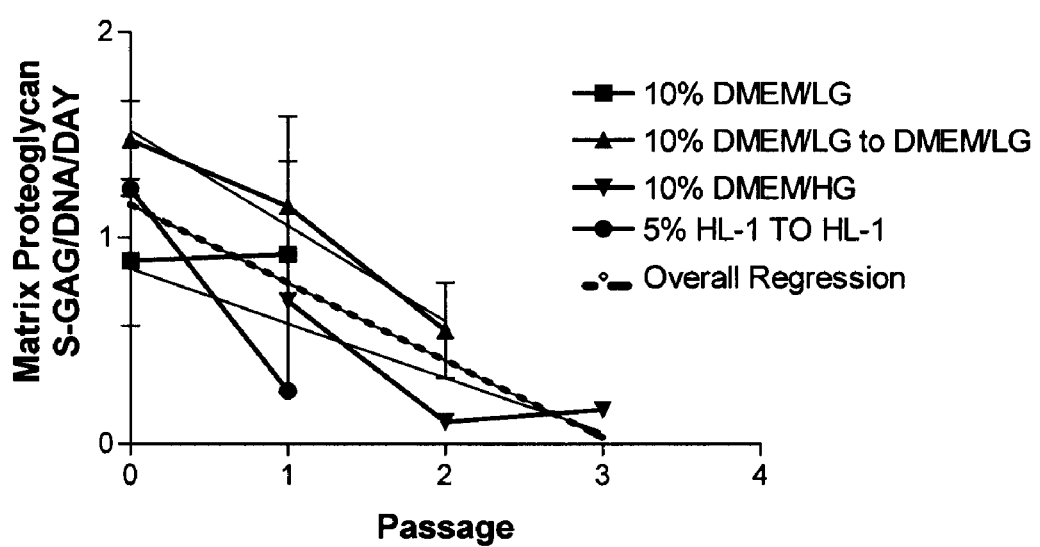
FIG. 1 is a graphic representation showing loss of chondrocyte differentiation potential as a function of passage number in serum containing medium. Young donor articular chondrocytes were expanded to passage three in serum containing medium using four different basal medium formulations. S-GAG, sulfated glycosaminoglycan; DNA, deoxyribose nucleic acid. DMEM, Dulbecco's modified Eagle's medium; LG, low glucose; HL-1, HL-1™ Complete Serum-free Medium from Cambrex (currently available as HL-1™ Serum-free Hybridoma Medium from Lonza Walkersville, Inc., Walkersville, Md.)

The term "chondrocytes" refers to cartilage-specific cells that give rise to normal cartilage tissue growth in vivo; these cells synthesize and deposit the supportive matrix (composed principally of collagen and proteoglycan) of cartilage.

The term "phenotype" refers to the observable characteristics at any level—physical, morphologic, biochemical or molecular—of a cell or tissue.

The term "neocartilage" refers to cartilage grown ex vivo and characterized by one or more of the following attributes: containing membrane phospholipids enriched in Mead acid but substantially depleted of linoleic or arachidonic acid, being substantially free of endothelial, bone and synovial cells, having a sulfated glycosaminoglycan (S-GAG) content of at least 40 μg/μg of DNA; being substantially free of types I, III and X collagen; containing a matrix substantially free of biglycan; having multiple layers of cells randomly arranged, rather than separated, into distinct zones of chondrocyte maturation; being enriched in high molecular weight aggrecan, or being characterized by having multiple layers of cells surrounded by a substantially continuous insoluble glycosaminoglycan and collagen-enriched hyaline extracellular matrix.

The term "hyaluronate substrate" refers to a substrate containing a hyaluronate mixture that is in large part comprised of a natural or synthetic, highly purified hyaluronate, such as sodium hyaluronate purified either from rooster combs or from bacterial fermentation. Hyaluronic acid is a polysaccharide composed of repeating disaccharide units of N-acetylglucosamine and glucuronic acid. Commercial HA is commonly its sodium salt form.

The term "cytokine" refers to a vast array of relatively low molecular weight, pharmacologically active proteins that are secreted by one cell for the purpose of altering either its own function(s) (autocrine effect) or those of adjacent cells (paracrine effect). Individual cytokines can have multiple biological activities. Different cytokines can also have redundant activity.

The term "FGF" indicates the fibroblast growth factor family of related proteins, which currently numbers 22 members (in humans, FGF-1-14 and FGF-16-23). "FGF-2" refers to the basic form of fibroblast growth factor (FGF). FGFs generally have a high affinity for heparan sulfate proteoglycans; interactions between FGF and heparin appear necessary for activation of each the FGF receptors (Ornitz and Itoh 2001). There are four FGFRs (FGFR1-4), each having many splice variants. An "active form" of an FGF polypeptide is a polypeptide that has significant (greater than 70%) homology to at least a portion of a conserved region of any FGF polypeptide and possesses the same activity as at least one of its homologues. The degree of activity can be greater or less than at least one of the homologues. In most cases, an internal core region containing approximately 28 highly conserved and six identical amino-acid residues can be identified, ten of which habitually interact with FGFRs (Ornitz, 2000 and Plotnikov et al., 2000).

The term "FGF-like activity" refers to an activity of a molecule, such as a polypeptide, that acts on at least one cell type in a similar manner as the cognate FGF molecule in at least one aspect. For example, a molecule having FGF-like activity can be substituted for FGF during the expansion of chondrocytes in the methods of the invention.

The term "TGF-β" indicates the transforming growth factor family of related proteins. TGF-β proteins are recognizable by C-terminus polypeptide homology and their signaling via the Similar to Mothers Against Decapentaplegic (SMAD) proteins after binding TGF-β receptors. Examples include TGF-β1-3, bone morphogenetic proteins (BMPs), etc. An "active form" of a TGF-β polypeptide is a polypeptide displaying significant (greater than 70%) homology to at least a portion of a conserved region of a TGF-β polypeptide and possesses the same activity as at least one of its homologues. The degree of activity can be greater or less than at least one of the homologues.

The term "TGF-β-like activity" refers to an activity of a molecule (such as a polypeptide) that acts on at least one cell type in a similar manner as a cognate TGF-β. molecule. For example, a molecule that signals via the SMAD proteins, regardless if the molecule has bound a TGF-β receptor or not, has TGF-β-like activity. TGF-β molecules stimulate synthesis of collagens, fibronectin, proteoglycans, tenascin, thrombospondin, plasminogen activator inhibitor-1 and tissue inhibitor of metalloprotease-1 proteins. A molecule having TGF-β-like activity, such as recombinant lactoferrin, can be substituted for TGF-β during the expansion of chondrocytes in the methods of the invention.

The term "low cell attachment" refers to a characteristic of chondrocyte culture conditions under which a majority of cells seeded onto a tissue substrate do not adhere to the tissue substrate.

The following embodiments are given as non-limiting examples of various ways to practice the invention.

In all embodiments, the underlying principle is to maintain native chondrocyte phenotype during ex vivo expansion by growing dissociated chondrocytes or chondroprogenitor cells under low attachment conditions that limit cell attachment and spreading. Low attachment conditions as described herein, including but not limited to use of certain substrate surfaces, have been found to support maintenance of chondrocyte morphology, phenotype and function during the process of expansion. The cartilaginous tissue produced therefrom is both biocompatible and safe for use in medical applications. Use of a low attachment substrate provides a microenvironment that more closely mimics that of native articular cartilage, resulting in retention of rounded cell shape and hyaline cartilage gene expression once the expanded cells exit the cell cycle. One example of a suitable low attachment condition is use of an HA-modified substrate, e.g. use of a polystyrene surface modified by covalent attachment of sodium hyaluronate. Chondrocytes adhere to immobilized HA via a cell surface glycoprotein receptor for hyaluronan (CD44) and can utilize the HA substrate to assemble the large proteoglycan aggregates typically found in normal, healthy articular cartilage.

High molecular weight HA (>400,000 MW) can be used as a substrate, or in solution, for in vitro expansion culture to increase total cell yield, while preventing loss of differentiated cell function. For example, the expansion of chondrocytes starting at low density on an HA modified substrate in chemically defined media significantly increases chondrocyte cell number. Similarly, chondrocytes expanded under other low attachment conditions such as use of HA in solution or use of a polystyrene substrate having an Ultra-Low Attachment coating such as those manufactured by Corning, produce an expanded population that maintains phenotype and morphology as determined and described elsewhere herein. Moreover, chondrocytes expanded in this manner retain their native chondrogenic differentiation potential to produce neocartilage tissue, and these cells or the neocartilage produced therefrom can be used for clinical application.

The present disclosure thus provides a method of producing chondrocytes under low attachment conditions such that chondrocytes remain rounded and loosely attached during the expansion process. In time, the chondrocytes are observed to undergo condensation, forming tissue aggregates or clusters. This unique method of expanding chondrocytes allows the cells to retain their functional activity after expansion. The invention also provides for kits for the expansion of chondrocytes. Therefore, this method serves to address the challenges identified in earlier cell-based approaches to articular cartilage repair.

Accordingly, one embodiment of the invention is a method in which isolated chondrocytes are expanded under low cell attachment conditions, for example on a substrate modified by covalent attachment of HA as described herein, or on an unmodified substrate using soluble HA in solution in the expansion medium, or on a substrate coated with a commercially available low cell attachment composition, such as those commercially available from Corning, Nunc, and Cell-Seed, Inc.

In yet another embodiment of the invention, a novel method for serially expanding chondrocytes in vitro on a substrate is provided. The method includes the steps of: isolating chondrocytes; growing the chondrocytes in a serum-free expansion medium containing cytokines and under low attachment conditions such as on a substrate modified to reduce cell attachment; and then using the expanded chondrocytes to produce hyaline-like cartilage tissue. The expanded population of cells is also well-suited for transplantation, and particularly for transplantation by injection, In a preferred method, chondrocytes are isolated from cartilage derived from immature donors, including neonatal, infant, or pre-adolescent donors for subsequent plating. Chondrocytes can be isolated by methods known in the art such as by sequential enzymatic digestion techniques (Adkisson et al., 2001). Isolated chondrocytes are then seeded onto a substrate under one of multiple possible low attachment conditions. Suitable low attachment conditions include e.g., use of a polystyrene substrate to which sodium hyaluronate is covalently attached, use of ultra low attachment plates such as those commercially available from Corning, Nunc, and CellSeed, Inc. (Hydrocell plates), use of tissue culture-treated polystyrene in the presence of serum-free expansion medium containing soluble HA, and use of tissue culture-treated polystyrene in the presence of serum-free expansion medium containing a low attachment agent other than HA, such as phosphatidyl choline.

Chondrocytes can be avian or mammalian chondrocytes, preferably human chondrocytes. Chondrocytes can be derived from transgenic animals that have been genetically engineered to prevent immune-mediated xenograft rejection (Sandrin et al., 1995; Sandrin et al., 1996 and Osman et al., 1997). Cartilage can be obtained from any tissue containing hyaline, elastic or fibro-cartilage.

In contrast to other methods of expanding chondrocytes known in the art, such as seeding cells on three dimensional scaffolds, further exogenous material beyond sodium hyaluronate is not required to retain differentiated chondrocyte morphology during expansion. The expansion method of the present invention provides for seeding chondrocytes in direct contact with an appropriate tissue culture surface. Although scaffold material is unnecessary, it can be used, for example in the case of polystyrene microcarrier beads.

In an illustrative embodiment, an expansion culture is produced by isolating immature chondrocytes, e.g., neonatal, infant or pre-adolescent, from donor articular cartilage and plating the dissociated cells onto a tissue culture substrate that is first modified via covalent attachment of sodium hyaluronate, or with a coating of any other chemical material that sufficiently reduces cell attachment and spreading, or using a serum-free expansion medium that contains HA, or another low-attachment agent such as phosphatidyl choline, in solution. Reduction of cell attachment and subsequent spreading is sufficient when a majority of cells in the starting population are observed not to attach to the substrate.

The isolated chondrocytes are then seeded directly on a tissue culture vessel in a suitable medium. Typically, a basal medium containing serum is used, but because serum has been observed to encourage the cells to de-differentiate (see, e.g. Example 1, FIG. 1), any serum-containing media is exchanged for a chemically defined serum-free expansion medium. "Chemically defined" refers to a serum-free medium, the chemical components of which are known. As used herein the term refers to that characteristic of expansion media used for expansion and also of tissue production media used.

Suitable substrates for expansion are any tissue culture plastics, such as virgin polystyrene, tissue-culture treated polystyrene or polycarbonate that can be modified to covalently attach hyaluronic acid. For embodiments of the method in which low attachment conditions are established using a substrate modified with HA, the only requirement for a suitable substrate is that it be amenable to modification with hyaluronic acid or N-acetylglucosamine, the natural building block to HA biosynthesis, or other polymers that restrict cell attachment and spreading. Preferably, hyaluronic acid or N-acetylglucosamine is covalently attached, although a covalent linkage is not necessary in most cases, except for direct attachment to polystyrene substrates.

The covalent modification of the substrate with HA provides a substrate that no longer is soluble in aqueous media and therefore maintains native chondrocyte phenotype during cytokine-mediated expansion of chondrocytes in serum-free expansion medium during two-dimensional culture. Hyaluronic acid recapitulates a cartilage microenvironment, whereas unmodified tissue culture plastic (polystyrene) does not. However, any other molecules that promote aggrecan assembly can be used, for example recombinant link protein.

Cross-linkers (Pierce, Rockford, Ill. "Cross-linkers"; product literature 2004).

Cross-linking two or more molecules is to covalently join them. Cross-linkers, cross-linking reagents, etc., have portions that react with specific functional groups, such as primary amines, sulfhydryls, carboxyls, etc. Most commonly used cross-linkers come in two forms: homobifunctional and heterobifunctional, although cross-linking reagents can have more than two reactive groups (e.g., trifunctional cross-linkers). Homobifunctional linkers have two identical reactive groups, whereas heterobifunctional cross-linkers have two different reactive groups. Homobifunctional cross-linkers are used in "single-stage" cross-linking. To take advantage of heterobifunctional cross-linkers, "sequential-stage" cross-linking procedures are used. Most commonly used cross-linkers have chemically reactive groups; however, cross-linkers with photoreactive groups can be used. An advantage of photoreactive groups is that they can form conjugates that otherwise cannot be formed using chemically reactive groups, although the efficiency of photoreactive groups can be low, most often 10%, sometimes up to 70%.

Common heterobifunctional cross-linkers include those that have amine-reactive succinimidyl ester at one end, and a sulfhydrylreactive group at the other. Another example is the carbodiimides, which are "zero-length" cross-linkers and effect direct coupling between carboxylates and primary amines.

The selection of a cross-linker is based on the target functional groups of the molecules to be cross-linked and the compatibility of the reaction to the application. The following characteristics are also considered: chemical specificity, spacer arm length, reagent solubility (and in the case of cells, membrane permeability), whether a homo- or hetero-bifunctional agent is appropriate or desired, chemically reactive or photoreactive groups, desirability of cleavable links after cross-linking, and whether the reagent can be conjugated to a label (e.g., a radiolabel). Over 300 cross-linkers are currently available; one of skill in the art recognizes that multiple approaches can be used to chemically cross-link HA to various substrates without significantly altering the ability of the HA to interact with cells, particularly in the case of developing reagents with spacer arms of increased length to enable the HA to be freely accessible in three-dimensional space.

The most important question, perhaps, is what functional groups are available for coupling. For example, if only lysine residues or N-terminal amino acids are available, a logical choice is NHS-ester homobifunctional cross-linkers. If one molecule has lysine residues and the other sulfhydryls, a maleimide NHS-ester cross-linker is appropriate. If only lysine residues are available on both molecules, modification to introduce sulfhydryls via the lysine residues on one molecule would allow for sequential coupling. If both molecules have free sulfhydryls, a homobifunctional sulfhydryl reactive cross-linker is appropriate. If carboxyl groups and amines are available, carbodiimide works well. Furthermore, if there are no readily reactive groups, a photoactivatible cross-linker can be used. If lysine residues are important for the functionality of the molecule, then a cross-linker that affects coupling through sulthydryls, carboxyls, or is nonspecific can be used. TABLE I lists some classes of reactive cross-linker groups and their functional group targets.

TABLE I

Reactive cross-linker groups and their functional group targets

| Reactive group (classes) | Functional group (classes) | Reactive group (classes) | Function group (classes) |
|---|---|---|---|
| aryl azide | non-selective (for primary amine) | Maleimide | sulfhydryl |
| carbodiimide hydrazide | amine/carboxyl oxidized carbohydrate | NHS-ester[1] PFP-ester[2] | amine amine |
| Hydroxymethyl prosphine | amine | Psoralen | thymine (photoreactive intercaltor) |
| Isocyanate | non-aqueous hydroxyl | vinyl sulfone | sulfhydryl, amine, hydroxyl |

[1]NHS, aminosuccinimidyl
[2]PFP, pentafluorophenyl

Spacer arm lengths can play an important role in the success of cross-linking, and usually requires empirical determination. Usually, a short spacer arm (4-8 A) is first used and then the success of cross-linking is assessed. If linking is poor, then cross-linkers with longer spacer arms can be explored. In some instances, a cleavable cross-linking agent is desirable; for example, if one would want to release a culture of chondrocytes intact with the HA substrate. TABLE II identifies an expanded list of applicable double-agent cross-linkers. TABLE II identifies an expanded list of applicable single-agent cross-linkers.

TABLE II

Double-agents cross-linkers

| Agent | Amines | Sulfhydryls | Carbohydrates | Photo-reactive | Carboxyls | Hydroxyl |
|---|---|---|---|---|---|---|
| p-Azidobenzoyl Hydrazide (ABH) | | | X | X | | |
| 3-[(2-Aminoethyl)dithio]propionic acid•HCl (AEDP) | X | | | | X | |
| N-[α-Maleimidoacetoxy] succinimide ester (AMAS) | X | X | | | | |
| N-5-Azido-2-nitrobenzoyloxysuccinimide (ANB-NOS) | X | | | X | | |
| N-[4-(p-Azidosalicylamido) butyl]-3'-(2'-pyridyldithio) propionamide (APDP) | | X | | X | | |
| p-Azidophenyl glyoxal monohydrate (APG) | | | | X | | |
| 4-[p-Azidosalicylamido butylamine (ASBA) | | | | X | X | |
| Bis-[β-(4-Azidosalicylamido)ethyl] disulfide (BASED) | | | | X | | |
| 1,4-Bis-maleimidobutane (BMB) | | X | | | | |
| Bis-Maleimidoethane (BMOE) | | X | | | | |
| N-β-Maleimidopropionic acid (BMPA) | X | X | | | | |
| N-[β-Maleimidopropionic acid] hydrazide•TFA (BMPH) | | X | X | | | |
| N-[β-Maleimidopropyloxy] succinimide ester (BMPS) | X | X | | | | |
| 1,8-Bis-Maleimidotriethyleneglycol (BM[PEO]₃) | | X | | | | |
| 1,11-bis-Maleimidotriethyleneglycol (BM[PEO]₄) | | X | | | | |
| Bis[2-Succinimidyloxycarbonyloxy)-ethylsulfone (BSOCOES) | X | | | | | |
| Bis[Sulfosuccinimidyl] suberate (BS3) | X | | | | | |
| 1,5-Difluora-2,4-dinitrobenzene (DFDNB) | X | | | | | |
| Dimethyl adipimidate•2 HCl (DMA) | X | | | | | |
| Dimethyl pimelimidate•2 HCl (DMP) | X | | | | | |
| Dimethyl suberimidate•2 HCl (DMS) | X | | | | | |
| 1,4-Di[3'-(2'-pyridyldithio)-propionamido]butane (DPDPB) | | X | | | | |
| Disuccinimidyl glutarate (DSG) | X | | | | | |
| Dithiobis[succinimidyl propionate] (DSP) | X | | | | | |
| Disuccinimidyl suberate (DSS) | X | | | | | |
| Disuccinimidyl tartrate (DST) | X | | | | | |
| Dimethyl 3,3'-dithiobispropionimidate•2 HCl (DTBP) | X | | | | | |
| Dithio-bis-maleimidoethane (DTME) | | X | | | | |
| 3,3'-Dithiobis[sulfosuccinimidyl propionate] (DTSSP) | X | | | | | |
| 1-Ethyl-3-[3-dimethylaminopropyl] carbodiimide Hydrochloride (EDC) | X | | | | X | |
| Ethylene glycol bis[succinimidylsuccinate] (EGS) | X | | | | | |
| N-ε-Maleimidocaproic acid) (EMCA) | X | X | | | | |
| N-[ε-Maleimidocaproic acid]hydrazide (EMCH) | | X | X | | | |
| N-[ε-Maleimidocaproyloxy] succinimide ester (EMCS) | X | X | | | | |
| N-[γ-Maleimidobutyryloxy] succinimide ester (GMBS) | X | X | | | | |
| 1,6-Hexane-bis-vinylsulfone (HBVS) | | X | | | | |

TABLE II-continued

| Double-agents cross-linkers | | | | | |
|---|---|---|---|---|---|
| N-κ-Maleimidoundecanoic acid (KMUA) | | X | X | | |
| N-[κ-Maleimidoundecanoic acid]hydrazide (KMUH) | | X | X | | |
| Succinimidyl-4[N-maleimidomethyl]-cyclohexane-1-carboxy-[6-amidocaproate] (LC-SMCC) | X | X | | | |
| Succinimidyl 6-[3-(2-pyridyldithio)-proionamido]hexanoate (LC-SPDP) | X | X | | | |
| m-Maleimidobenzoyl-N-hydroxysuccinimide ester (MBS) | X | X | | | |

| | Cleavable by (○) | | | | Iodinat-able |
|---|---|---|---|---|---|
| Agent | Thiols | Base | Periodate | Hydroxyl-amine | |
| p-Azidobenzoyl Hydrazide (ABH) | | | | | N |
| 3-[(2-Aminoethyl)dithio]propionic acid•HCl (AEDP) | ○ | | | | N |
| N-[α-Maleimidoacetoxy] succinimide ester (AMAS) | | | | | N |
| N-5-Azido-2-nitrobenzoyloxysuccinimide (ANB-NOS) | | | | | N |
| N-[4-(p-Azidosalicylamido) butyl]-3'-(2'-pyridyldithio) propionamide (APDP) | ○ | | | | Y |
| p-Azidophenyl glyoxal monohydrate (APG) | | | | | N |
| 4-[p-Azidosalicylamido butylamine (ASBA) | | | | | Y |
| Bis-[β-(4-Azidosalicylamido)ethyl] disulfide (BASED) | ○ | | | | Y |
| 1,4-Bis-maleimidobutane (BMB) | | | | | N |
| Bis-Maleimidoethane (BMOE) | | | | | N |
| N-β-Maleimidopropionic acid (BMPA) | | | | | N |
| N-[β-Maleimidopropionic acid] hydrazide•TFA (BMPH) | | | | | N |
| N-[β-Maleimidopropyloxy] succinimide ester (BMPS) | | | | | N |
| 1,8-Bis-Maleimidotriethyleneglycol (BM[PEO]$_3$) | | | | | N |
| 1,11-bis-Maleimidotriethyleneglycol (BM[PEO]$_4$) | | | | | N |
| Bis[2-Succinimidyloxycarbonyloxy)-ethylsulfone (BSOCOES) | | ○ | | | N |
| Bis[Sulfosuccinimidyl] suberate (BS3) | | | | | N |
| 1,5-Difluora-2,4-dinitrobenzene (DFDNB) | | | | | N |
| Dimethyl adipimidate•2 HCl (DMA) | | | | | N |
| Dimethyl pimelimidate•2 HCl (DMP) | | | | | N |
| Dimethyl suberimidate•2 HCl (DMS) | | | | | N |
| 1,4-Di[3'-(2'-pyridyldithio)-propionamido]butane (DPDPB) | ○ | | | | N |
| Disuccinimidyl glutarate (DSG) | | | | | N |
| Dithiobis[succinimidyl propionate] (DSP) | ○ | | | | N |
| Disuccinimidyl suberate (DSS) | | | | | N |
| Disuccinimidyl tartrate (DST) | | | ○ | | N |
| Dimethyl 3,3'-dithiobispropionimidate•2 HCl (DTBP) | ○ | | | | N |
| Dithio-bis-maleimidoethane (DTME) | ○ | | | | N |
| 3,3'-Dithiobis[sulfosuccinimidyl propionate] (DTSSP) | ○ | | | | N |
| 1-Ethyl-3-[3-dimethylaminopropyl] carbodiimide Hydrochloride (EDC) | | | | | N |
| Ethylene glycol bis[succinimidylsuccinate] (EGS) | | | | ○ | N |
| N-ε-Maleimidocaproic acid) (EMCA) | | | | | N |
| N-[ε-Maleimidocaproic acid]hydrazide (EMCH) | | | | | N |
| N-[ε-Maleimidocaproyloxy] succinimide ester (EMCS) | | | | | N |
| N-[γ-Maleimidobutyryloxy] succinimide ester (GMBS) | | | | | N |
| 1,6-Hexane-bis-vinylsulfone (HBVS) | | | | | N |
| N-κ-Maleimidoundecanoic acid (KMUA) | | | | | N |
| N-[κ-Maleimidoundecanoic acid]hydrazide (KMUH) | | | | | N |
| Succinimidyl-4[N-maleimidomethyl]-cyclohexane-1-carboxy-[6-amidocaproate] (LC-SMCC) | | | | | N |
| Succinimidyl 6-[3-(2-pyridyldithio)-proionamido]hexanoate (LC-SPDP) | ○ | | | | N |
| m-Maleimidobenzoyl-N-hydroxysuccinimide ester (MBS) | | | | | N |

TABLE III

| Single-agents cross-linkers | | | | | | | |
|---|---|---|---|---|---|---|---|
| | Reactive toward (X) | | | | | | Cleavable by (○) |
| Agent | Amines | Sulf-hydryls | Carbo-hydrates | Photo-reactive | Carboxyl | Hydroxyl | Thiol |
| 4-[N-Maleimidomethyl] cyclohexane-1-carboxyl-hydrazide•½ dioxane(M$_2$C$_2$H) | | X | X | | | | |
| 3-Maleimidophenyl boronic acid(MPBH) | | X | X | | | | |
| Methyl N-succinimidyl adipate(MSA) | X | | | | | | |
| N-Hydroxysuccini midyl-4-azidosalicylic acid(NHS-ASA) | X | | | X | | | |
| 3[2-Pyridyldithio]propionl hydrazide(PDPH) | | X | X | | | | ○ |

TABLE III-continued

Single-agents cross-linkers

| Agent | | | | | |
|---|---|---|---|---|---|
| N-[p-Maleimidophenyl] isocyanate(PMPI) | | X | | X | ○ |
| N-Succinimidyl [4-azidophenyl]-1,3'-dithiopropionate (SADP) | X | | X | | ○ |
| Sulfosuccinimidyl 2-[7-axido-4-methylcoumarin-3-acetamido]ethyl-1,3'-dithiopropionate(SAED) | X | | X | | ○ |
| Sulfosuccinimidyl 2-[m-azido-o-nitro-benzamido]ethyl-1,3'-dithiopropionate(SAND) | X | | X | | ○ |
| N-Succinimidyl 6-[4'-azido-2'-nitro-phenylamino] hexanoateSANPAH | X | | X | | |
| Sulfosuccinimidyl-2-[p-azido-salicylamido]ethyl-1,3'-dithiopropionate(SASD) | X | | X | | ○ |
| N-Succinimidyl S-acetylthioacetate(SATA) | X | X | | | |
| N-Succinimidyl S-acetylthiopropionate(SATP) | X | X | | | |
| Succinimidyl 3-[bromoacetamido] propionate(SBAP) | X | X | | | |
| Sulfosuccinimidyl-[perfluoroazido-benzamido]-ethyl-1,3'-dithiopropionate(SFAD) | X | | X | | ○ |
| N-Succinimidyl iodoacetate(SIA) | X | X | | | |
| N-Succinimidyl[4-iodoacetyl] aminobenzoate(SIAB) | X | X | | | |
| Succinimidyl 4-[N-maleimidomethyl]-cyclohexane-1-carboxylate](SMCC) | X | X | | | |
| Succinimidyl 4-[p-maleimidophenyl] butyrate(SMPB) | X | X | | | |
| Succinimidyl-6-[(β-maleimidopropionamido) hexanoate](SMPH) | X | X | | | |
| 4-Succinimidyloxy carbonyl-methyl-α [2-pyridyldithio] toluene(SMPT) | X | X | | | ○ |
| N-Succinimidyl 3-[2-pyridyldithio] propionate(SPDP) | X | X | | | ○ |
| Bis[2-(Sulfosuccinimido oxycarbonyloxy)-ethyl]sulfone(Sulfo-BSOCOES) | X | | | | |
| Disulfosuccinimidyl tartrate(Sulfo-DST) | X | | | | |
| Ethylene glycol bis [sulfosuccinimidylsuccinate](Sulfo-EGS) | X | | | | |
| N-[ε-Maleimidocaproyloxy]sulfosuccinimide ester(Sulfo-EMCS) | X | X | | | |
| N-[γ-Maleimidobutyryloxy]sulfo-succinimide ester(Sulfo-GMBS) | X | X | | | |
| N-Hydroxysulfosuccinimidyl-4-azidobenzoate(Sulfo-HSAB) | X | | X | | |
| N-[κ-Maleimidoundecanoyloxy]-sulfosuccinimide ester(Sulfo-KMUS) | X | X | | | |
| Sulfosuccinimidyl 6-[3'-(2-pyridyldithio)-propionamido]hexanoateSulfo-LC-SPDP | X | X | | | ○ |
| m-Maleimidobenzoyl-N-hydroxysulfo-succinimide ester(Sulfo-MBS) | X | X | | | |
| Sulfosuccinimidyl [4-azidosalicylamido]-hexanoate(Sulfo-NHS-LC-ASA) | X | | X | | |
| Sulfosuccinimidyl [4-azidophenyldithio]-propionate(Sulfo-SADP) | X | | X | | ○ |
| Sulfosuccinimidyl 6-[4'-azido-2'-nitro-phenylamino] hexanoate(Sulfo-SANPAH) | X | | X | | |
| Sulfosuccinimidyl [4-iodoacetyl]aminobenzoate(Sulfo-SIAB) | X | X | | | |
| Sulfosuccinimidyl 4-[N-maleimidomethyl]-cyclohexane-1-carboxylate(Sulfo-SMCC) | X | X | | | |
| Sulfosuccinimidyl 4-[p-maleimidophenyl]-butyrate(Sulfo-SMPB) | X | X | | | |
| Sulfosuccinimidyl-6-[α-methyl-α-(2-pyridyldithio) toluamido] hexanoate(Sulfo-LC-SMPT) | X | X | | | ○ |
| Sulfosuccinimidyl [2-6-(biotinamido)-2-(p-azidobenamido)-hexanoamido]ethyl-1,3'-dithioproionate(Sulfo-SBED) | X | | X | | ○ |
| N-Succinimidyl-[4-vinylsulfony] benzoate(SVSB) | X | X | | | |
| N-[ε-Trifluoroacetylcaproyloxy] succinimide ester(TFCS) | X | | | X | |
| β-[Tris (hydroxymethyl) phosphino]-propionic acid (betaine)(THPP) | X | | | | |
| Tris-[2-maleimidoethyl] amine(TMEA) | | X | | | |
| Tris-succinimidyl aminotriacetate(TSAT) | X | | | | |

| Agent | Cleavable by (○) | | | | Latent functional group |
|---|---|---|---|---|---|
| | Base | Periodate | Hydroxyl-amine | Iodinat-able | |
| 4-[N-Maleimidomethyl] cyclohexane-1-carboxyl-hydrazide•½ dioxane(M₂C₂H) | | | | N | |
| 3-Maleimidophenyl boronic acid(MPBH) | | | | N | |
| Methyl N-succinimidyl adipate(MSA) | | | | N | CO—OH |
| N-Hydroxysucci midyl-4-azidosalicylic acid(NHS-ASA) | | | | Y | |
| 3[2-Pyridyldithio]propionl hydrazide(PDPH) | | | | N | |
| N-[p-Maleimidophenyl] isocyanate(PMPI) | | | | N | |
| N-Succinimidyl [4-azidophenyl]-1,3'-dithiopropionate (SADP) | | | | N | |
| Sulfosuccinimidyl 2-[7-axido-4-methylcoumarin-3-acetamido]ethyl-1,3'-dithiopropionate(SAED) | | | | N | |
| Sulfosuccinimidyl 2-[m-azido-o-nitro-benzamido]ethyl-1,3'-dithiopropionate(SAND) | | | | N | |
| N-Succinimidyl 6-[4'-azido-2'-nitro-phenylamino] hexanoateSANPAH | | | | N | |
| Sulfosuccinimidyl-2-[p-azido-salicylamido]ethyl-1,3'-dithiopropionate(SASD) | | | | Y | |
| N-Succinimidyl S-acetylthioacetate(SATA) | | | | N | —SH |
| N-Succinimidyl S-acetylthiopropionate(SATP) | | | | N | —SH |
| Succinimidyl 3-[bromoacetamido] propionate(SBAP) | | | | N | |
| Sulfosuccinimidyl-[perfluoroazido-benzamido]-ethyl-1,3'-dithiopropionate(SFAD) | | | | N | |

TABLE III-continued

Single-agents cross-linkers

| | | | | |
|---|---|---|---|---|
| N-Succinimidyl iodoacetate(SIA) | | | | N |
| N-Succinimidyl[4-iodoacetyl] aminobenzoate(SIAB) | | | | N |
| Succinimidyl 4-[N-maleimidomethyl]-cyclohexane-1-carboxylate](SMCC) | | | | N |
| Succinimidyl 4-[p-maleimidophenyl] butyrate(SMPB) | | | | N |
| Succinimidyl-6-[(β-maleimidopropionamido)hexanoate](SMPH) | | | | N |
| 4-Succinimidyloxy carbonyl-methyl-α [2-pyridyldithio] toluene(SMPT) | | | | N |
| N-Succinimidyl 3-[2-pyridyldithio] propionate(SPDP) | | | | N |
| Bis[2-(Sulfosuccinimido oxycarbonyloxy)-ethyl]sulfone(Sulfo-BSOCOES) | ○ | | | N |
| Disulfosuccinimidyl tartrate(Sulfo-DST) | | ○ | | N |
| Ethylene glycol bis [sulfosuccinimidylsuccinate](Sulfo-EGS) | | | ○ | N |
| N-[ε-Maleimidocaproyloxy]sulfosuccinimide ester(Sulfo-EMCS) | | | | N |
| N-[γ-Maleimidobutyryloxy]sulfo-succinimide ester(Sulfo-GMBS) | | | | N |
| N-Hydroxysulfosuccinimidyl-4-azidobenzoate(Sulfo-HSAB) | | | | N |
| N-[κ-Maleimidoundecanoyloxy]-sulfosuccinimide ester(Sulfo-KMUS) | | | | N |
| Sulfosuccinimidyl 6-[3'-(2-pyridyldithio)-propionamido]hexanoateSulfo-LC-SPDP | | | | N |
| m-Maleimidobenzoyl-N-hydroxysulfo-succinimide ester(Sulfo-MBS) | | | | N |
| Sulfosuccinimidyl [4-azidosalicylamido]-hexanoate(Sulfo-NHS-LC-ASA) | | | | Y |
| Sulfosuccinimidyl [4-azidophenyldithio]-propionate(Sulfo-SADP) | | | | N |
| Sulfosuccinimidyl 6-[4'-azido-2'-nitro-phenylamino] hexanoate(Sulfo-SANPAH) | | | | N |
| Sulfosuccinimidyl [4-iodoacetyl]aminobenzoate(Sulfo-SIAB) | | | | N |
| Sulfosuccinimidyl 4-[N-maleimidomethyl]-cyclohexane-1-carboxylate(Sulfo-SMCC) | | | | N |
| Sulfosuccinimidyl 4-[p-maleimidophenyl]-butyrate(Sulfo-SMPB) | | | | N |
| Sulfosuccinimidyl-6-[α-methyl-α-(2-pyridyldithio) toluamido] hexanoate(Sulfo-LC-SMPT) | | | | N |
| Sulfosuccinimidyl [2-6-(biotinamido)-2-(p-azidobenamido)-hexanoamido]ethyl-1,3'-dithioproionate(Sulfo-SBED) | | | | N |
| N-Succinimidyl-[4-vinylsulfony] benzoate(SVSB) | | | | N |
| N-[ε-Trifluoroacetylcaproyloxy] succinimide ester(TFCS) | | | | NH$_2$ |
| β-[Tris (hydroxymethyl) phosphino]-propionic acid (betaine)(THPP) | | | | N |
| Tris-[2-maleimidoethyl] amine(TMEA) | | | | N |
| Tris-succinimidyl aminotriacetate(TSAT) | | | | N |

Sodium periodate can be used to create reactive aldehyde groups for crosslinking of glycosaminoglycans to a variety of structures containing available primary amines through the formation of a stable Schiff base. Glycosaminoglycans such as chondroitin sulfate, dextran and sodium hyaluronate have been modified using such procedures. Most recently, Liu et al., 2003 described the preparation of hyaluronate-polyaldehydes to form a tissue engineering scaffold useful for bone repair (Healos®) (Liu et al., 2003).

In this way, activated hyaluronate-polyaldehyde is prepared by oxidizing sodium hyaluronate with sodium periodate, followed by extensive dialysis. The density of reactive aldehydes (formyl groups) on the hyaluronate polymer can be controlled by altering the reaction time, and can be monitored quantitatively using a modification of the bicinchoninic acid method (Hermanson GT Bioconjugate Techniques, San Diego, Academic Press, Inc., 1996, p 622). Consequently, an alternative method for cross linking sodium hyaluronate to polystyrene surfaces involves Schiff base formation between the sulfonamide created in the first step with the reactive aldehydes of periodate-oxidized HA. The lyophilized HA-polyaldehyde is stable at 4° C. (dark storage). An aqueous solution of the polyaldehyde is added to the modified polystyrene surface and allowed to react either at room temperature or at 37° C., depending on the extent of cross-linking desired. Unreacted material is then removed by aspiration, and the plates are washed extensively in distilled water and culture medium prior to seeding with cells.

In the isolations of cells from tissues for the methods of the invention, care should be taken during enzymatic digestion to optimize total cell yield and viability. Traditionally, chondrocytes have been isolated from cartilage tissue by sequential enzymatic digestion, using a nonspecific protease followed by a mixture of collagenase and hyaluronidase. Unfortunately, most preparations of proteolytic enzymes used for research purposes contain significant levels of endotoxin, as well as a variety of undesirable proteolytic activities that can damage cell membrane proteins, leading to apoptotic cell death.

Liberase™ Blendzyme preparations were developed by Roche Diagnostics Corporation (Indianapolis, Ind.) to address the increasing demand for proteases with characterized enzymatic activity and purity. From a regulatory perspective, these enzymes are preferred materials for use in the manufacturing of tissue engineered medical products. Blendzyme 2 contains a combination of collagenase and neutral protease activity that works well for harvesting primary chondrocytes from articular cartilage. Reduced levels of the same enzyme are preferred when chondrocytes are released from a culture substrate.

Blendzymes are blends of purified collagenases I and II and a neutral protease. The collagenases are purified from the fermentation of *Clostridium histolyticum*. Currently four formulations are available. Blendzyme 1 contains the neutral protease dispase, which is purified from *Bacillus polymyxa* fermentation. Blendzymes 2, 3 and 4 contain the neutral protease thermolysin, purified from *Bacillus thermoproteolyticus* fermentation. The methods for purifying and blending these components for Blendyme preparation have been described in U.S. Pat. Nos. 5,753,485 and 5,830,741. The use of Blendzyme mixes can be optimized using the criteria presented in TABLE IV.

TABLE IV

Optimizing Blendzyme ™ Use

| Observation 1 | Observation 2 | Possible cause | Recommendation |
| --- | --- | --- | --- |
| Low cell viability | Dissociation very rapid | Enzyme concentration too high | Reduce enzyme concentration by 50%. |
| | | Blendzyme number too high | Move down one Blendzyme level, keep initial concentration. |
| | Dissociation very slow | Enzyme concentration too low | Increase enzyme concentration by 50%. |
| | | Blendzyme number too low | Move up one Blendzyme level, keep initial concentration. |
| Impaired cell function | Cell viability >80%, cell yield is reasonable | Enzyme concentration too high | Reduce enzyme concentration by 25%. |
| | | Blendzyme number too high | Move down one Blendzyme level, keep initial concentration. |
| Low cell yield | Cell viability >80% | Enzyme concentration too low | Increase enzyme concentration by 25-50%. |
| | | Blendzyme number too low | Move up one Blendzyme level, keep initial concentration. |
| | Cell viability <80% | Enzyme concentration too high | Reduce enzyme concentration by 50%. |
| | | Blendzyme number too high | Move down one Blendzyme level, keep initial concentration. |
| | | Mechanical (shear) force is excessive | Reduce shear force in all aspects of dissociation. Treat tissue gently. |
| Released cells clump in gelatinous stringy form | Cell yield and viability are acceptable | DNA release, subsequent to cell lysis, is causing clumping | More prevalent in some tissues. If cell viability is acceptable, add DNase to dissociation mixture. |
| | Cell yield or viability are reduced | Mechanical (shear) force is excessive | Reduce shear force in all aspects of dissociation. Treat tissue gently. |

While Blendzymes are preferred, any method that safely releases the cells can be used, including those that use chelating agents, with and without enzymes. Ethylenediaminetetraacetic acid (EDTA) and ethylene-bis(oxyethylenenitrilo) tetraacetic acid (EGTA) are two such common reagents that can be used singly, or in combination.

In an illustrative embodiment of the invention, chondrocytes are isolated from immature donors such as neonatal, infants, or pre-adolescents, and expanded on a substrate surface material, such as polystyrene, that is covalently modified via covalent attachment of sodium hyaluronate, or on a substrate under other suitably low attachment conditions as described elsewhere herein. The expanded cells are subsequently grown in a chemically defined serum-free tissue production medium to produce neocartilage for cartilage repair. (As set forth elsewhere herein, a "chemically defined" medium, whether for expansion or tissue production, is a serum-free medium the chemical components of which are specified.) Alternatively, the resulting expanded population of cells can be frozen for future transplantation, for example by injection, or can be frozen in a cryopreservation step before a second phase of expansion. A population of cells that has undergone two phases of expansion may also be frozen in a second cryopreservation step prior to being seeded under appropriate culture conditions for tissue growth and extracellular matrix production.

Chondrogenic Progenitor Stem Cells.

Other cells that are suitable for the methods of the invention include those isolated from placenta (Kogler et al., 2004), bone marrow mesenchymal stromal cells (Mackay et al., 1998; Kavalkovick et al., 2002), adipose stromal cells (Huang et al., 2004), synovium (DeBari et al., 2004) and periosteum (DeBari et al., 2001).

The serum-free tissue production medium can also comprise vitamin C, ascorbate, exogenous autocrine growth factors or conditioned growth media as described below. When culturing cells according to the methods of the invention, the presence of vitamin C (ascorbic acid) is preferred. Vitamin C can be supplied in any active form, as a free acid or as a salt. Examples include calcium ascorbate, magnesium ascorbate, sodium ascorbate and L-ascorbic acid 2-phosphate or an esterified derivative thereof. The concentration to be used can be determined empirically, depending on the source of the cells, but usually, concentrations range from $5.6 \times 10^{-4}$ g/L to 0.1 g/L when supplied as sodium ascorbate. Likewise, the serum free tissue production medium can comprise dexamethasone, or a salt derivative thereof. Dexamethasone enhances SOX 9 expression and presumably will increase the capacity for cartilage matrix production by the expanded cells (Sekiya et al., 2001; Malpeli et al., 2004).

The cell culture can be grown under suitable culture conditions such as growing the cell culture at 37° C. in a humidified atmosphere with the addition of 2-10% $CO_2$, preferably 5%.

Doubling Time

Depending on various factors, including initial plating density, quality of the expansion media, genetic factors inherent in the cells, temperature, the quality of HA and its application to the substrate etc., the doubling time for a particular group of cells may vary. The doubling time observed for chondrocytes that are maintained as described in the present invention is generally 3 to 4 days, when plated at a density of $3 \times 10^4$/$cm^2$. When the length of time for expansion culture is increased to day 14 and 17, as many as 4-6 chondrocyte population doublings can be achieved. In contrast, the same cells grown in serum-supplemented media are limited by contact inhibition and produce no greater than two population doublings. A preferred defined expansion medium used in the present invention is HL-1, a proprietary formulation containing insulin-transferrin-selenium-complex as its only source of protein (HL-1™ of Lonzo Walkersville, Inc., (formerly Cambrex), Walkersville, Md.). The serum-free expansion medium containing cytokines is either completely or partially replaced every three to four days after the initial seed.

Optimal media selection depends on the cell type; that media used to culture the cells usually represents a preferred option. Examples of suitable culture media include Iscove's Modified Dulbecco's Medium (IMDM), Dulbecco's Modified Eagle's Medium (DMEM), Minimal Essential Medium Eagle (MEM), Basal Medium Eagle (BME), Click's Medium, L-15 Medium Leibovitz, McCoy's 5A Medium, Glasgow Minimum Essential Medium (GMEM), NCTC 109 Medium, Williams' Medium E, RPMI-1640, Medium 199, Ham's F12 and SFM (Gibco).

A medium specifically developed for a particular cell type/line other than chondrocytes may not be useful in the practice of this invention, particularly if it contains epidermal growth factor which is reported to induce chondrogenic dedifferentiation (Yoon et al., 2002).

In some cases, a protein can be added to support the cells, such as various albumins, including bovine serum albumin. If desired, the media can be further supplemented with reagents that limit acidosis of the cultures, such as buffer addition to the medium (such as N,N-bis(2-hydroxyethyl)-2-aminoethanesulfonic acid (BES), bis(2-hydroxyethyl)amino-tris(hydroxymethyl)methane (BIS-Tris), N-(2-hydroxyethyl)piperazine-N'3-propanesulfonic acid (EPPS or HEPPS), glyclclycine, N2-hydroxyethylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris (hydroxymethyl)-aminom-ethane (Tris), etc.). Frequent medium changes and changes in the supplied $CO_2$ (often approximately 5%) concentration can also be used to control acidosis.

The sources of various materials used in the specific laboratory examples are as follows:

Materials—Dulbecco's Modified Eagle's medium (DMEM) with added L-glutamine, sodium pyruvate, and glucose (either 1.0 g/liter [LG] or 4.5 g/liter [HG]), fetal bovine serum (FBS) and antibiotic (100 times) (penicillin G, sodium (10,000 units) and streptomycin sulfate (25 mg/ml in normal saline) were obtained from Life Technologies, Inc. (Grand Island, N.Y.).

Pronase-E (Type XIV, from *Streptomyces griseus*), hyaluronidase (type VIII, bovine testes), N-tris [hydroxymethyl] methyl-2-aminoethanesulfonic acid (TES), and MILLEX-GS syringe sterilization filters were obtained from Sigma Chemical Company (St. Louis, Mo.).

Collagenase (CLS 4) was purchased from Worthington Biochemicals (Freehold, N.J.). Tissue-culture dishes (35 mm dia., 100 mm dia, 12 and 24 well clusters) and bottle top sterilization filter units (type CA) were obtained from Costar Corporation (Cambridge, Mass.).

Bovine serum albumin (fraction V, fatty acid-free) was from Calbiochem (San Diego, Calif.). HL-1™ Complete Serum-free Medium was obtained from Cambrex (now Lonzo Walkersville, Inc.).

In another preferred embodiment, chondrocyte expansion ex vivo is for cartilage repair. In this embodiment, cartilage is removed from a non-damaged cartilage area around a damage site and digested with collagenase. The resulting chondrocytes are expanded on the modified substrate of the invention, then injected or implanted into the cartilage defect site. Similarly, marrow stromal fibroblasts can be isolated from a normal area adjacent a bone defect, expanded ex vivo as described and administered at the site of a bone defect.

The expansion of chondrocytes of the invention (U.S. Pat. No. 6,617,161) containing platelet derived growth factor (PDGF), epidermal growth factor (EGF), fibroblast growth factor (FGF), and bone morphogenetic proteins results in the loss of two main cartilage-specific phenotypic markers, type II collagen and proteoglycan aggrecan, which are critical components for cartilage assembly and repair. Discontinued expression of these molecules indicates that the cells have undergone phenotypic dedifferentiation. Yoon et al., 2000 recently demonstrated that EGF promotes loss of native chondrocyte phenotype.

Chondrocytes cultured on unmodified polystyrene develop a fibroblastic appearance, displaying an elongated cell shape relative to their native rounded morphology. The characterization of phenotypic markers in the expanded chondrocyte population is necessary to establish the potential functional properties of the manipulated cells. Food and Drug Administration (FDA)/Center for Biologics Evaluation and Research (CBER) requires that protocols relating to ex vivo expansion of articular chondrocytes for repair of joint surfaces prove that the expanded cell populations are very similar to the native chondrocytes. This can be assessed by measuring mRNA expression levels of aggrecan core protein and type II collagen at the end of the expansion protocol or after neocartilage production by any appropriate method, including molecular methods (e.g., Northern blotting, RT-PCR) and biochemical methods (e.g., immunoprecipitation; affinity chromatography) or immunocytochemical methods (e.g., ELISA or immunofluorescence-activated cell sorting (FACS)). Those protocols that detect the target proteins are preferred.

Any bioactive molecule that improves the proliferation, differentiation potential or quality of the resulting regenerated tissue can be used according to the present invention.

Expansion of cells under low attachment conditions, such as on an HA-modified substrate, also improves the efficiency of transfection of nucleic acids into the cells. Typically, nucleic acid transfer is carried out during monolayer expansion, and cells in active mitosis are more amenable to DNA transduction. Therefore, applications where tissue engineering techniques are combined with gene therapy can be utilized in accordance with the teachings of the present invention. For example, cells can be transfected with a vector that confers resistance to a variety of biological and chemical compounds, such as antibiotics, cytokines and inflammatory agents, or with a vector that result in the overexpression and synthesis of a particular growth factor or matrix component.

Implantation

Dissociated cells isolated from the expansion process of the present invention are typically grown without scaffold support to create a three-dimensional tissue for cartilage repair (U.S. Pat. No. 6,235,316). However, cells expanded via this method can be implanted in combination with suitable biodegradable, polymeric matrix or hydrogel to form new cartilage tissue. There are two forms of matrices which can be used: a polymeric hydrogel formed of a material, such as fibrin or alginate, having cells suspended therein, and a fibrous matrix having an interstitial spacing between about 40 and 200 microns. Preferred polymeric matrices are those that degrade in about one to two months after implantation; such as polylactic acid-glycolic acid copolymers (U.S. Pat. No. 5,716,404). The matrices can be seeded prior to implantation or implanted, allowed to vascularize, then seeded with cells. (See, e.g., Cima et al., 1991; Vacanti et al., 1988; and Vacanti et al., 1988).

Other materials, such as bioactive molecules that enhance vascularization of the implanted tissue and/or inhibit fibrotic tissue ingrowth can be implanted with the matrix to enhance development of more normal tissue.

EXAMPLE 1

Loss of Chondrocyte Phenotype by Serial Expansion in Serum Containing Media

Chondrocytes, regardless of tissue origin, rapidly lose the ability to synthesize cartilage specific macromolecules with serial expansion in vitro (Homicz et al., 2002; Mandl et al., 2002). Although juvenile chondrocytes are thought to better retain the ability to synthesize matrix macromolecules than adult articular chondrocytes, the following experiment was performed to determine the effect of serial expansion on chondrocyte matrix synthesis using chondrocytes derived from immature articular cartilage. A variety of media containing serum were evaluated to demonstrate the deleterious effects of serum on chondrocyte differentiation potential.

Sixteen (16) different donor cell populations were isolated from cadaveric articular cartilage ranging in age from newborn to three years. Four different basal medium formulations containing the indicated amount of fetal bovine serum were used: 10% DMEM/LG, 10% DMEM/LG to DMEM/LG, 10% DMEM/HG and 5% HL-1 to HL-1. T-75 flasks containing $3 \times 10^4$ cells/cm$^2$ were seeded and cultured for twenty-one days with complete exchange of growth medium occurring twice per week. Chondrocytes were released from the cultures by enzymatic dissociation, and total cell number and viability were estimated with fluorescent detection using a Guava Personal Cell Analysis system (Guava Technologies, Inc, Hayward, Calif.). Dissociated cells ($1 \times 10^6$ viable cells) were subsequently seeded in 48 well plates using HL-1 complete serum-free medium (formerly available from Cambrex, now HL-1™ Serum-free Hybridoma Medium available from Lonza Walkersville, Inc., Walkersville, Md.) to produce neocartilage as described by Adkisson et al, 2001. Cultures were harvested for biochemical composition analysis on day 45 of culture.

FIG. 1 is a graphic representation showing loss of chondrocyte differentiation potential as a function of serial expansion in serum-containing medium. Two of the groups were expanded through two passages to a maximum of 2.8 population doublings (nearly an eight-fold increase in total cell number). A marked loss in the ability of juvenile articular chondrocytes to produce cartilageneous proteoglycan was observed. An overall regression line was plotted from the data which demonstrated a greater than 70% reduction in chondrocyte matrix synthesis after nearly three population doublings, relative to non-expanded chondrocytes derived from the same individuals.

Similar to what has been reported to occur in adult articular chondrocytes, these data illustrate that chondrocytes derived from young tissue donors rapidly lose the ability to assemble matrix proteoglycans after serial expansion in monolayer culture when maintained in various growth media containing fetal bovine serum ranging from 5-10% (v/v). Thus it appears that serum-derived factors, in contrast to donor age, determines in large part the extent to which chondrocytes dedifferentiate in vitro during monolayer culture, resulting in a significant loss in neocartilage matrix formation potential.

EXAMPLE 2

Method for Covalent Immobilization of Sodium Hyaluronate on Polystyrene Surfaces To improve the efficiency with which chondrocytes can be expanded in vitro without loss of native chondrocyte phenotype, juvenile chondrocytes were grown on a modified substrate prepared via covalent attachment of high molecular weight sodium hyaluronate to polystyrene. It was hypothesized that immobilized sodium hyaluronate, in contrast to unmodified tissue culture plastic, would provide a microenvironment that could more closely mimic that of native articular cartilage. The following method for chemical modification of polystyrene with sodium hyaluronate is a modification of that originally described by Turley and Roth (Turley and Roth, 1979).

Figure 2:
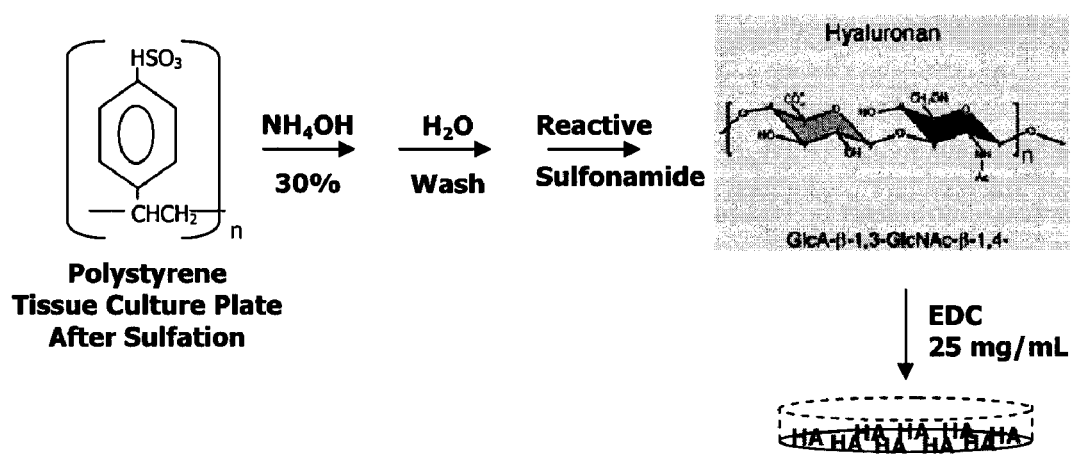
FIG. 2 is a representation of the chemical methods used to covalently attach HA to a polystyrene surface, originally described by Turley and Roth (Turley and Roth, 1979). $HSO_3$, hydrogen sulfite ion; $NH_4OH$, liquid ammonia; $H_2O$, water; HA, hyaluronic acid; EDC, 3-(3-dimethylaminopropyl) carbodiimide hydrochloride.

In FIG. 2, the virgin polystyrene plates were treated with sulfuric acid at 37° C. for two hours. After removing the sulfuric acid and extensive washing of the plates in deionized distilled water, the reactive sulfonamide was created by adding aqueous ammonium hydroxide (24 hours at room temp.). The base was removed, and the plates again were washed extensively with water. Finally, a solution of high molecular weight sodium hyaluronate (HyluMed, Medical Grade, Genzyme Advanced Biomaterials, Cambridge, Mass.; 5 mg/mL in water) was cross-linked to the reactive sulfonamide using 3-(3-dimethylaminopropyl)carbodiimide (EDC) hydrochloride (48 hours at 37° C.). This process is depicted in FIG. 2. Prior to initiating the expansion cultures, hyaluronate/EDC solution was removed by aspiration, and the tissue culture plates were washed extensively in deionized distilled water, followed by two washes in HL-1 Complete Serum-free Medium (Cambrex).

EXAMPLE 3

Chondrocyte Phenotype Retained by Serial Expansion on Ha-Coated Plastic in Serum-Free Medium Chondrocytes derived from a six week-old subject were taken through two passages using plates that were modified by the method illustrated in Example 2. Differentiation potential of the expanded chondrocytes was assessed after enzymatic dissociation and estimation of total cell number and viability. A proprietary serum-free differentiation medium, developed at Isto Technologies, Inc, was used to stimulate chondrocyte differentiation. In contrast to other methods, such as that described by Martin et al. (U.S. Pat. No. 6,582, 960), this medium contains neither TGF β nor dexamethasone to enhance chondrogenic differentiation potential, and the only protein component in this formulation is recombinant human insulin (Serologicals Corporation, Milford, Mass.).

Figure 3:
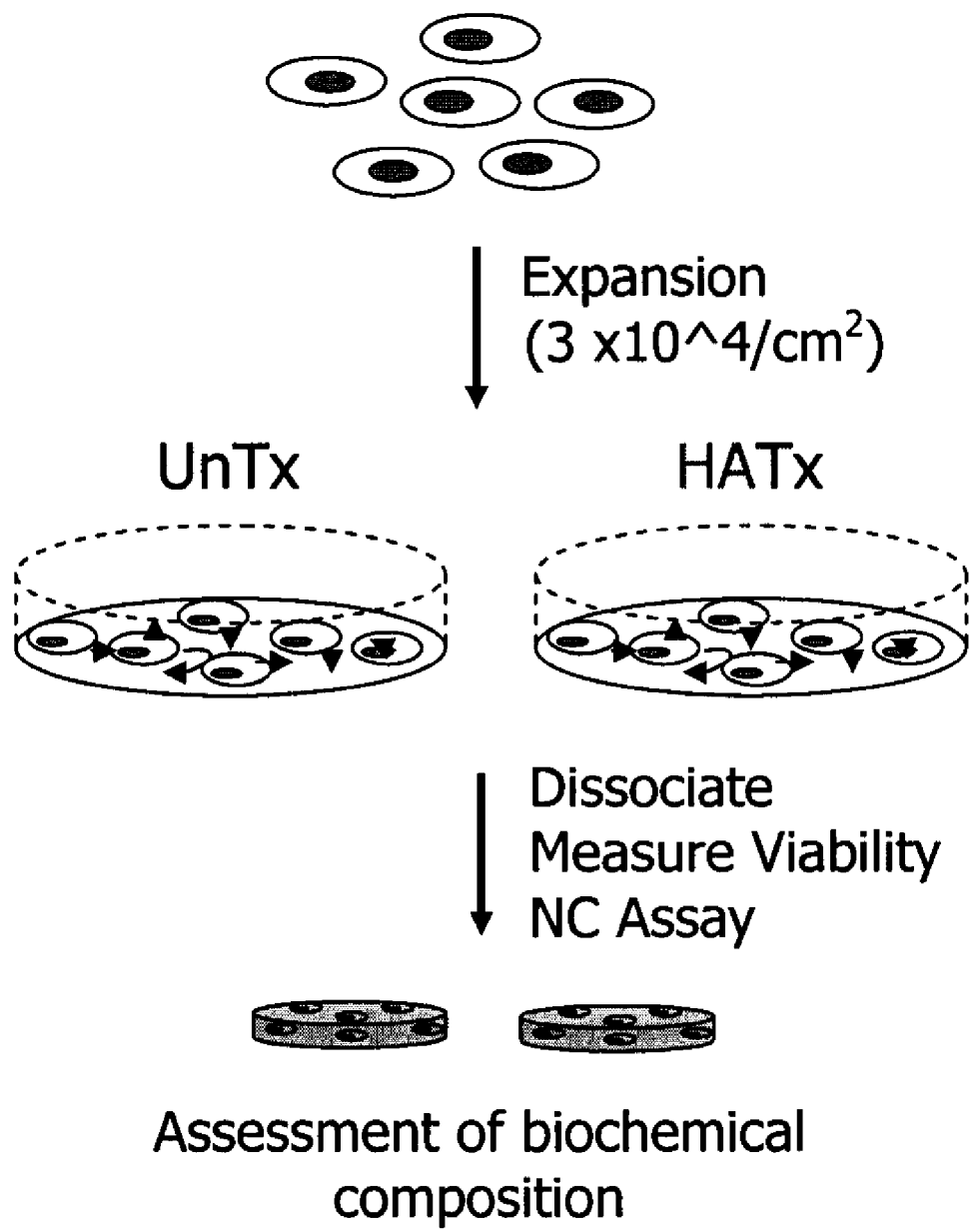
FIG. 3 is a graphic representation of the current method of cytokine-mediated chondrocyte expansion on a sodium hyaluronate substrate and subsequent growth of neocartilage. UnTx, unmodified tissue culture plastic; HATx, HA modified tissue culture plastic; NC Assay, neocartilage functional assay.

FIG. 3 shows a schematic representation of the process of cytokine-mediated chondrocyte expansion in which covalent attachment of sodium hyaluronate serves as a substrate for maintenance of chondrocyte phenotype during expansion. Primary chondrocytes are isolated, washed and resuspended at a final density of $3\times10^4$ cells/cm$^2$ in HL-1 Complete Serum-free Medium containing 100 ng/mL FGF-2 and 20/ng/mL TGF-β and vitamin C. Control and HA-treated plates were harvested after 14-17 days of expansion using Blendzyme 2 as described in Example 7. An aliquot of the dissociated cells was plated in differentiation medium to assess neocartilage formation potential, while the remaining cells underwent serial expansion. Neocartilage was harvested from differentiation cultures between day 28 and 45 for measurement of total proteoglycan, DNA and collagen content in the neocartilage matrix. These values were compared to those obtained for neocartilage prepared from non-expanded chondrocytes using the same methods. The total cumulative increase in chondrocyte number was 85-fold or 6.5 population doublings.

Figure 4:
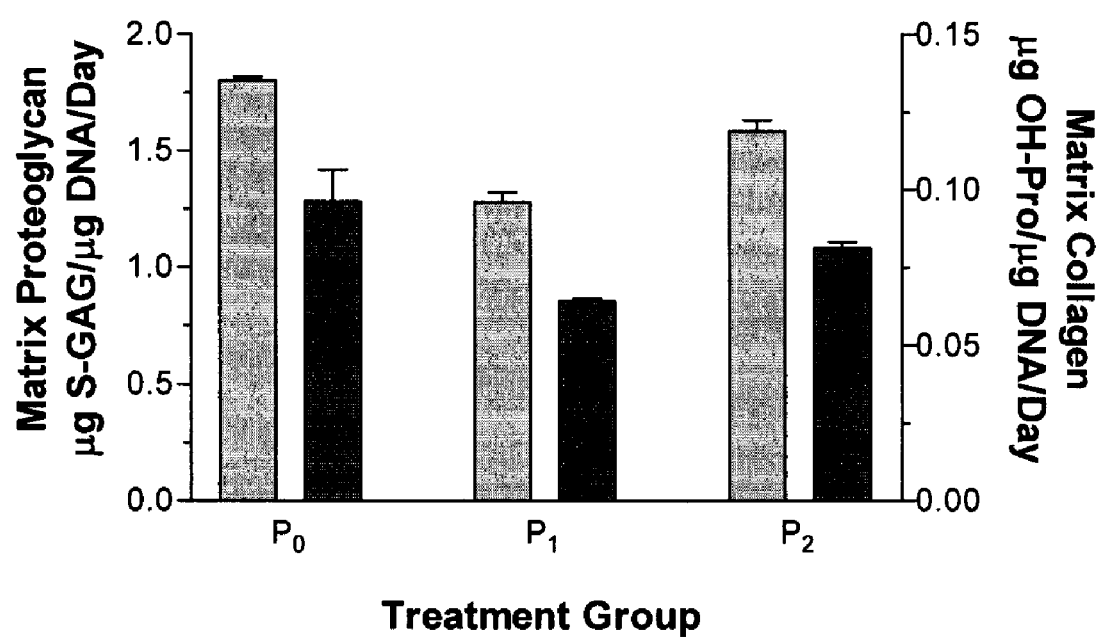
FIG. 4 shows the biochemical composition of NC grafts that were produced from chondrocytes that were expanded on HA modified polystyrene in defined serum-free medium containing basic fibroblast growth factor (bFGF), transforming growth factor beta (TGFβ) and vitamin C as compared to freshly isolated chondrocytes. Chondrocytes were derived from young donor articular cartilage.

FIG. 4 illustrates the biochemical composition data that was collected on grafts produced from the freshly dissociated unpassaged cells (P0) and passage two cells (P2). Neocartilage grafts were initiated at a density of $1\times10^6$ cells/well in untreated 48-well plates using freshly dissociated cells and cells from each successive passage to P2. The rates of glycosaminoglycan (S-GAG/DNA/Day) and collagen (hydroxyproline/DNA/Day) synthesis are plotted on the left- and right-hand axis, respectively. Data represent the mean of replicates of four (4) to five (5).+/−STD.DEV. Estimated population doublings for each expansion was 2.25 and 4.25 at passage one cells P1 and P2, respectively, at day 14 and 17 of culture.

Young donor chondrocytes that were expanded on HA-modified polystyrene in defined serum-free medium containing FGF and TGF β showed minimal loss of differentiation potential relative to the freshly isolated chondrocytes. As shown in FIG. 4, the proteoglycan content of P1 and P2 neocartilage is within 78-88% of that of the primary cultures, indicating that little change in the rate of extracellular matrix synthesis occurred as a result of the expansion conditions. In contrast to chondrocyte expansion in 10% fetal bovine serum (see data Example 1), these levels reflect a three- to four-fold increase in total matrix production over cells that were expanded in a variety of serum-containing media. In fact, neocartilage grafts produced from young donor chondrocytes that were expanded on HA-modified plastic in a chemically defined growth medium were found to make rigid tissue discs that were easily manipulated ex vivo with forceps.

In a separate experiment, growth of expanded chondrocytes (differentiation assay) on HA-modified plastic resulted in a 25% increase in total matrix production (both sulfated glycosaminoglycan and collagen), relative to growth on unmodified tissue culture plastic. These data suggest that immobilization of HA to the culture surface prior to chondrocyte differentiation directs neocartilage formation, resulting in greater production of cartilage extracellular matrix and supports the earlier work of Kujawa et al. (1986). In contrast to Kujawa et al., the present work illustrates that there is no dependence on size of HA polymer.

With the ultimate goal of establishing in vitro conditions for chondrocyte expansion that are efficient, reproducible and which result in maintenance of normal chondrocyte phenotype, this example illustrates that a plastic surface modified by covalent attachment of sodium hyaluronate limits chondrocyte spreading during expansion and retains the functional properties of the expanded chondrocytes.

EXAMPLE 4

Chondrocytes Expanded on Covalently Bound Sodium Hyaluronate Maintain Rounded Morphology and Native Function This example demonstrates that chondrocytes cultured on an HA-coated substrate in defined medium results in maintenance of native chondrocyte phenotype by retaining rounded cell shape and function.

Human P1 chondrocytes, derived from a five year-old, having first been expanded on unmodified plastic in the presence of cytokine, were used in this pilot experiment to determine if immobilized HA could restore both rounded chondrocyte morphology and the functional properties of the cells after enzymatic dissociation. Thirty-five mm diameter polystyrene dishes were modified via covalent attachment of sodium HA as described. $2\times10^5$ chondrocytes were harvested from an expansion of primary cells and subsequently seeded onto HA-modified and unmodified polystyrene surfaces for further expansion in HL-1 Complete Serum-free Medium (Cambrex) containing 2 ng/mL TGF β-2 and 10 ng/mL variant human FGF-2 (ProChon, Ltd., Rehovat, Israel) and vitamin C. Cultures were harvested on day 10 for enumeration and estimation of viability using Guava ViaCount® reagents. Greater than 2.5 population doublings were achieved at day 10 of culture.

Figure 5A:
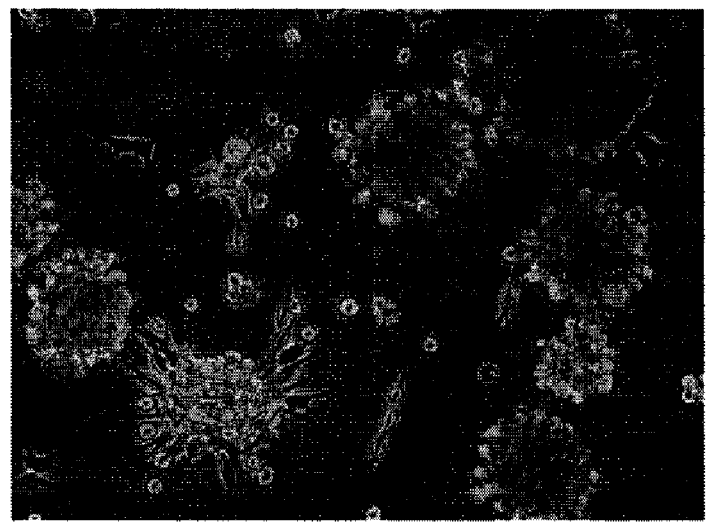
FIGS. 5A and 5B show the effect of covalently bound sodium hyaluronate on chondrocyte morphology.

FIG. 5A illustrates that chondrocytes expanded in the presence of cytokines on HA-modified polystyrene form chondrocyte islands or aggregates in which the chondrocytes appear to maintain a rounded morphologic appearance. Formation of these cartilage aggregates is reminiscent of the condensation of mesenchymal tissue which normally occurs in vivo during skeletal development (Singley and Solursh, 1981). The relative opacity of the chondrocyte aggregates suggests that the chondrocytes continue to actively synthesize extracellular matrix components. Thus, chondrocytes grown on the HA modified surface formed clusters of cells that retained a rounded morphology, characteristics of the chondrocyte phenotype.

Figure 5B:
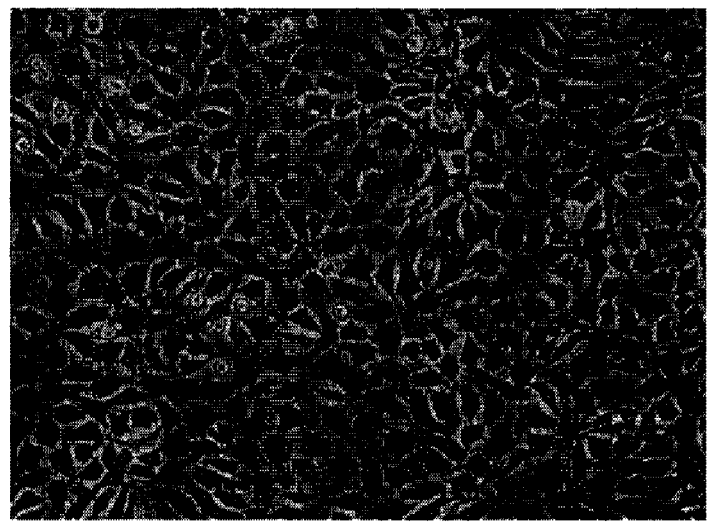

In contrast, the same cells expanded under identical conditions on unmodified plates exhibited a flattened, cobblestone appearance (FIG. 5B). In these cultures, chondrocyte expansion potential appeared to be limited by contact inhibition.

Figure 6:
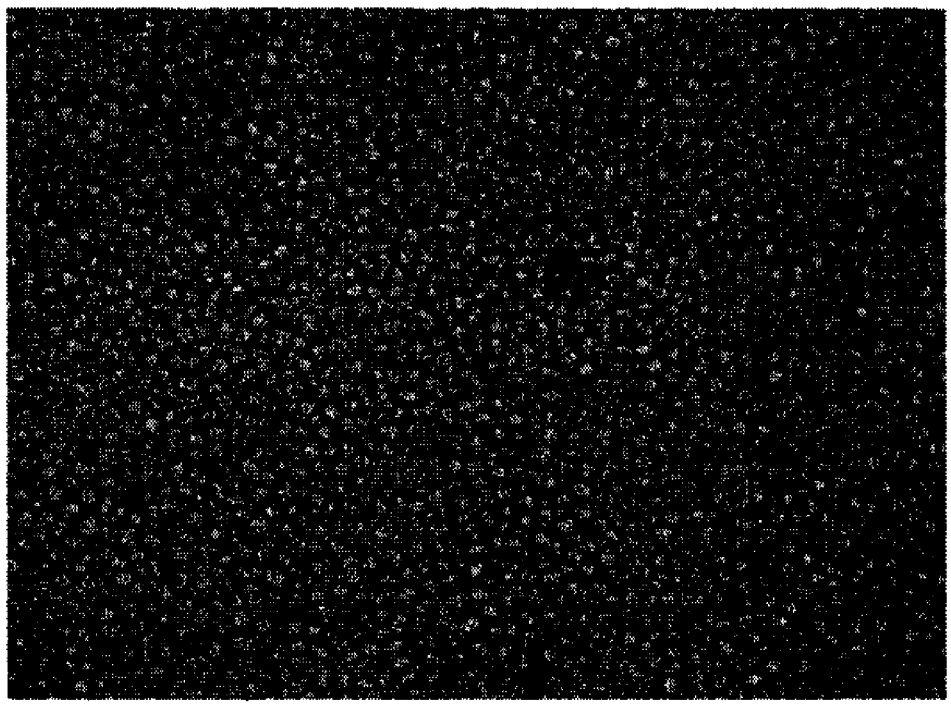
FIG. 6 is a photomicrograph of neocartilage produced from passage two chondrocytes (P2) that were expanded on HA modified polystyrene in HL-1 ™ Complete Serum-free Medium containing variant fibroblast growth factor-2 (vFGF-2), transforming growth factor beta-2 (2 ng/mL)) [ProChon Ltd.] and TGF-β-2 (10 ng/mL).
Figure 7:
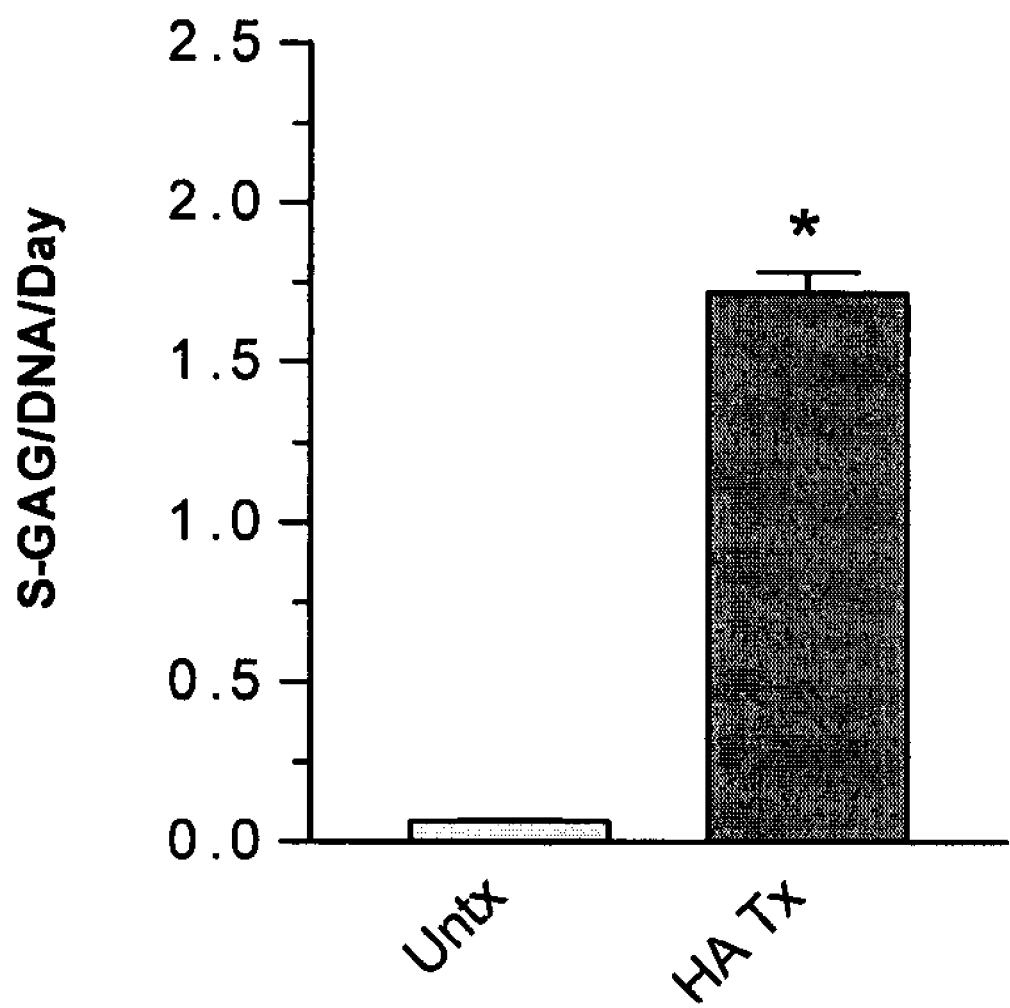
FIG. 7 is a graphic representation showing the biochemical composition of newly synthesized NC matrix from chondrocytes that were expanded on HA modified polystyrene versus control cells that were expanded on unmodified polystyrene. S-GAG, sulfated glycosaminoglycan; DNA, deoxyribose nucleic acid; UnTx, unmodified tissue culture plastic; HATx, HA modified tissue culture plastic. *, denotes significance ($P<0.05$) relative to grafts that were produced with cells that were derived from expansion in the absence of HA-modified substrate.

Chondrocytes from each of these groups were subsequently passaged by dissociation in collagenase and hyaluronidase and seeded ($1\times10^6$ per well) into 48-well culture dishes (unmodified) to measure the capacity to which the P2 cells synthesize neocartilage matrix. Using chemically defined conditions to optimize matrix production (see example 3) in the absence of three-dimensional scaffolds or pellet culture, the chondrocytes were grown for 45 days, at which time they were harvested for biochemical composition analysis. FIG. 6 shows a photomicrograph of neocartilage obtained at Day 10 of culture, illustrating the rounded morphologic appearance of P2 cells that were harvested from expansion culture on HA-modified polystyrene. Chondrocytes expanded by this method and placed in differentiation culture displayed a rounded morphologic appearance characteristic of freshly dissociated chondrocytes. FIG. 7 compares the biochemical composition of newly synthesized NC matrix obtained for chondrocytes that were expanded on HA modified plastic to that of the same cells that were expanded on unmodified polystyrene.

Substrate containing covalently bound HA appears to preserve native chondrocyte morphology (rounded phenotype) during neocartilage tissue formation, and more importantly, to restore chondrocyte extracellular matrix synthesis in expanded cells to a level that approached that of the primary culture population (approximately 1.75 to 2 µg S-GAG/µg DNA/Day).

EXAMPLE 5

Characterization of Chondrocyte Phenotype at the Molecular Level

Maintenance of native chondrocyte phenotype in cells that had been expanded on HA-modified polystyrene was confirmed at the molecular level by gene expression analysis. Chondrocytes harvested at each passage in scale-up experiments were used for RNA isolation, and the relative mRNA levels corresponding to a set of cartilage-specific extracellular matrix macromolecules and the cartilage transcription factor, SOX 9, were analyzed using semi-quantitative reverse transcriptase polymerase chain reaction (RT-PCR).

Figure 8:
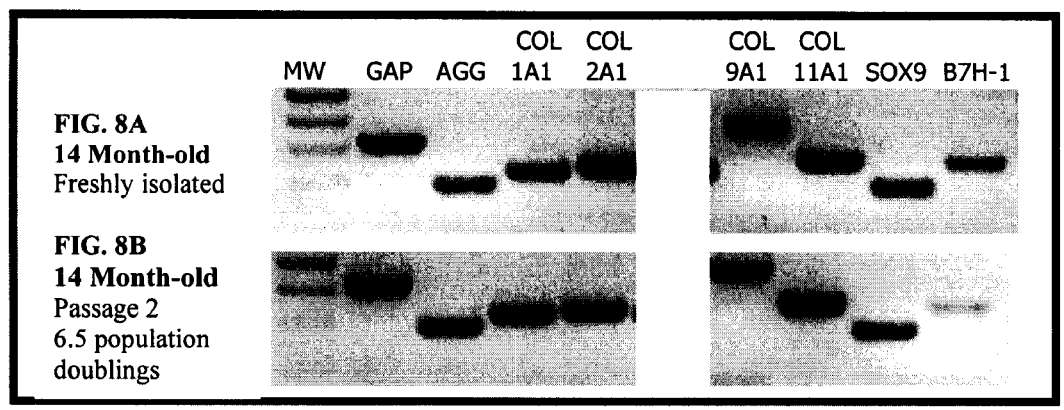
FIG. 8, in two parts.

FIGS. 8A and 8B show representative gene expression profiles obtained for P0 and P2 chondrocytes that were harvested from the cells used in Example 4 above. Note that P2 cells have gone through a total of 6.5 population doublings. No discernable difference was observed in the pattern of gene expression obtained from freshly dissociated chondrocytes (upper panel) and the same cells after 6.5 population doublings (lower panel). mRNA levels for SOX 9 and B7-H1 remained unchanged after serial expansion. B7-H1 is the putative negative regulator of alloreactivity that is thought to maintain the immune privilege status of chondrocytes in vitro and in vivo (Adkisson et al., unpublished observations).

Figure 9:
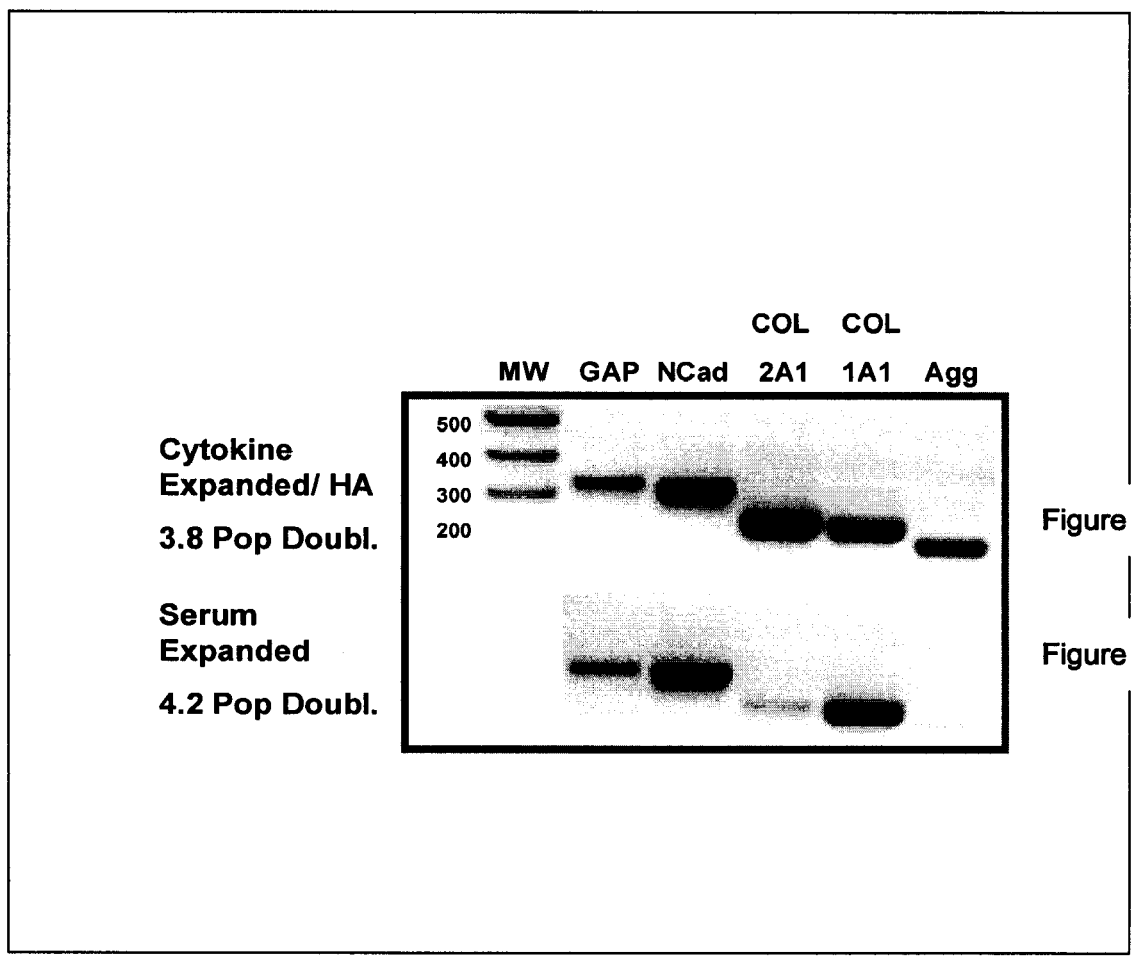
FIG. 9, in two parts.

Even though the P2 cells have gone through 6.5 cumulative population doublings, a point at which prior studies have described significant changes in cartilage-specific gene expression (Dell'Accio et al., 2001), these cells maintained a pattern of gene expression that was substantially the same as P0 cells. With little change in the level of SOX9 gene expression in the P2 chondrocytes, it was expected that the expression of genes controlling collagen and aggrecan core protein synthesis would show little change in expression level. This hypothesis was confirmed by gene expression profile analysis of mRNA encoding for aggrecan core protein and collagen types II, IX and XI, as well as collagen type I, which is associated with fibro-cartilage formation. It is noteworthy that a significant loss in the level of aggrecan core protein and type II collagen gene expression was observed in the same population of chondrocytes that were serially expanded in HL-1 medium containing 10% FBS and vitamin C (FIG. 9A and FIG. 9B). As shown in Example 1, chondrocytes expanded in serum containing media also lose their functional capacity to synthesize and assemble neocartilage matrix.

This experiment showed that chondrocyte expansion on a hyaluronate-modified substrate represents a preferred microenvironment that results in maintenance of native phenotype as demonstrated by morphological analysis of chondrocyte cell shape and gene expression profiling. By contrast, chondrocytes that were expanded in serum containing medium showed marked changes in mRNA levels for aggrecan core protein and type II collagen, two macromolecules essential for cartilage formation and repair.

EXAMPLE 6

Chondrocyte Expansion Using Alternative Low Attachment Conditions that Support Maintenance of Native Chondrocyte Phenotype Previous examples 4 and 5 demonstrate the unique ability of a modified polystyrene surface to support chondrocyte expansion during anchorage-independent growth, i.e. under a low attachment condition. Chondrocytes maintained under low attachment conditions undergo extensive growth while retaining their native rounded morphological appearance and the ability to synthesize engineered tissues ex vivo. Confirmation of phenotype retention was demonstrated at both the biochemical and molecular level.

In this example, the purpose was to demonstrate that different methods can be used to achieve the same result of limiting chondrocyte attachment and spreading during ex vivo expansion, thus allowing cells to maintain phenotype and hyaline cartilage gene expression during the process of expansion. Three different conditions were used for comparison: Group A, covalently bound HA; Group B, soluble HA added to the expansion medium at 1 mg/mL using tissue culture-treated plastic ware, and Group C, Ultra Low Attachment plates manufactured by Corning. Juvenile articular chondrocytes were plated at a density of $3\times10^4$ cells/cm$^2$ in T-75 tissue culture flasks containing HL-1 supplemented medium as defined in earlier examples. Expansion cultures were maintained to day 21, with supplementation or exchange of fresh medium occurring every 3 to 4 days. The expanded population of cells was then dissociated for harvest using Liberase™ Blendzyme 2, at which time the number of viable cells was established for each condition prior to cryopreservation. Chondrocytes obtained from each of the three conditions studied were found to undergo between 3 and 4 population doublings. These passage one cells were subsequently used to generate neocartilage discs in 48-well plates. The resulting neocartilage discs were harvested between day 40 and 45 of culture for biochemical analysis. The morphologic appearance of cells grown in each of the low attachment conditions was monitored microscopically, and the biochemical composition of the resulting neocartilage was assessed using standard assays.

Figure 10:
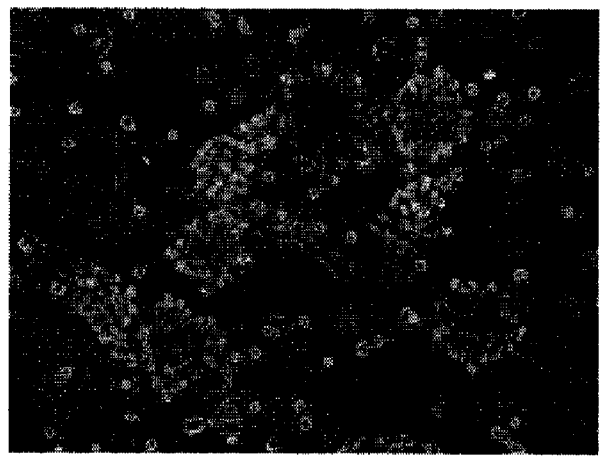
FIG. 10, in three parts.
Figure 10:
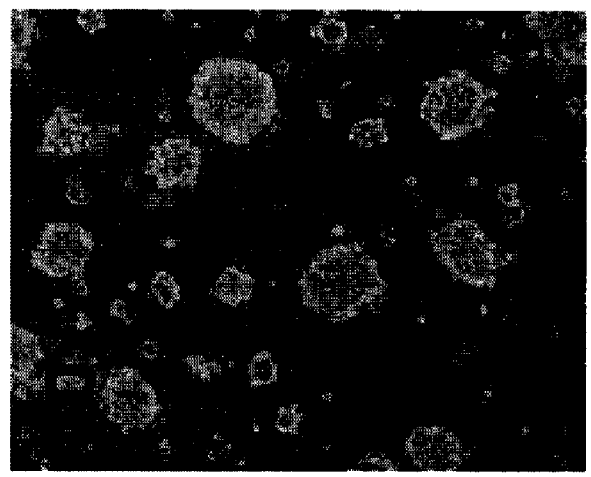
Figure 10:
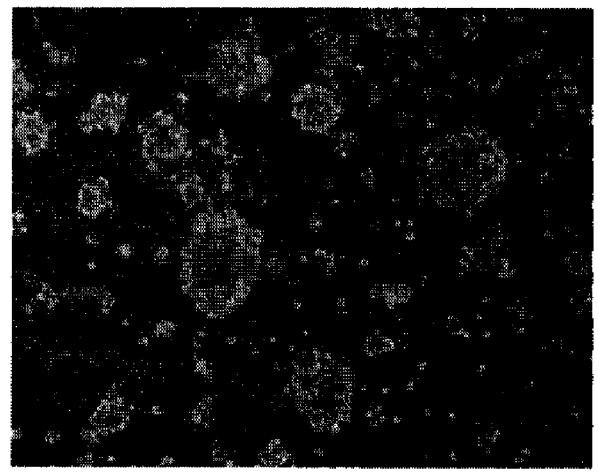

FIG. 10 shows a comparison of the morphologic appearance of culture-expanded chondrocytes imaged at 100× prior to harvest. Arrows indicate suspended clusters observed for each expansion condition. Nearly all cells cultured in each condition were observed to maintain a rounded morphologic appearance and do not attach and spread on the substrate. A)

polystyrene plastic ware was modified via covalently attachment of HA; B) soluble HA added to the expansion medium—unmodified regular tissue culture plastic; C) ultra low attachment plates used for the expansion substrate (purchased from Corning). In each case, a similar rounded morphology and clustering of cells was observed.

Figure 11:
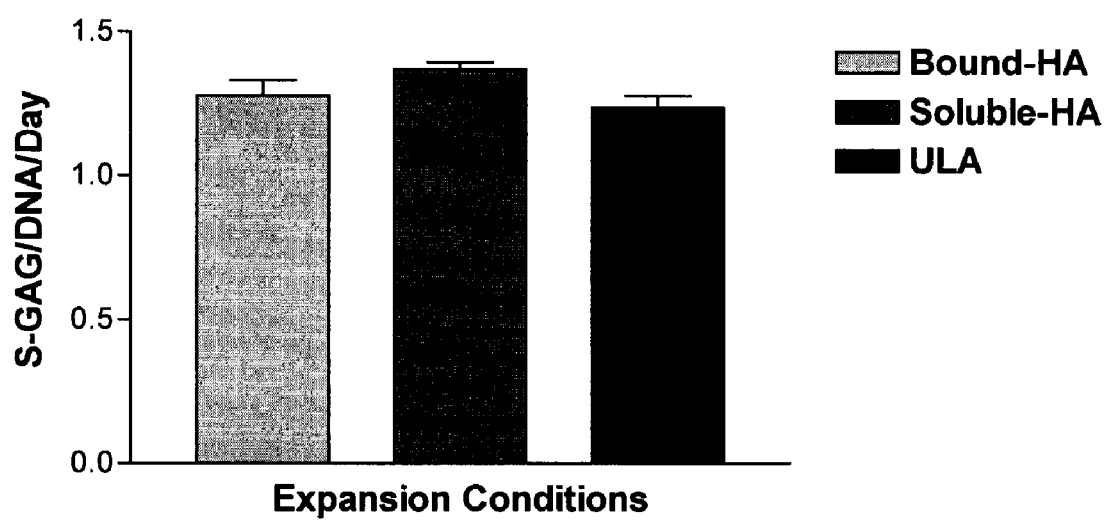
FIG. 11 is a graphic representation of the rate of proteoglycan synthesis by culture-expanded chondrocytes following neocartilage growth on polycarbonate inserts.

FIG. 11 shows a comparison of the rate of proteoglycan synthesis measured for triplicate samples of neocartilage produced using cells obtained by each expansion condition. Data were normalized to DNA content and the number of days in culture. Equivalent rates of matrix proteoglycan production were observed for each of the expanded chondrocyte populations, with means ranging between 1.24 and 1.37 micrograms of S-GAG per microgram of DNA per day of culture. No statistically significant difference in the rate of proteoglycan synthesis was observed among the populations of chondrocytes subsequently used to produce neocartilage.

These data illustrate that various methods can be used to sufficiently limit chondrocyte attachment and spreading during ex vivo expansion, such that in each method, the expanded population of cells maintains the native morphologic appearance of chondrocytes during ex vivo expansion. Maintenance of cell shape during expansion is important because, as has been shown elsewhere herein, these chondrocytes retain the ability to synthesize an extensive extracellular matrix upon mitogen removal.

To further demonstrate equivalence of each of the methods used above to generate expanded chondrocytes with retained functional capacity, quantitative real-time PCR was used to assess the level of gene expression for a select group of genes normally expressed by articular chondrocytes. Type I collagen, which is reported to show marked increases in gene expression by dedifferentiated chondrocytes, was also measured to confirm the hyaline nature of the neocartilage produced by cells grown using the conditions identified above for Groups B and C, e.g. soluble HA combined with regular tissue culture plastic and ultra low adhesion plates (ULA), respectively. RNA was isolated from neocartilage that had been generated ex vivo from cells that had undergone >6 population doublings at Passage 2 (P2). Table V sets forth the relative level of gene expression for articular chondrocytes harvested from a two month-old donor. Relative gene expression for Col2A1, Aggecan core protein, SOX9 and Col1A1 is normalized to the expression of the housekeeping gene, GAPDH (GAP).

TABLE V

Relative Gene Expression for Chondrocytes and Fibroblasts

| Cell Source | Relative Gene Expression | | | |
|---|---|---|---|---|
| | Col2A1/ GAP | Aggrecan/ GAP | SOX9/ GAP | Col1A1/ GAP |
| Freshly Dissociated Chondrocytes | 87.52 | 4.450 | 0.326 | 1.304 |
| Neocartilage- Soluble HA (P2) | 131.8 | 7.635 | 0.232 | 0.205 |
| Neocartilage- ULA (P2) | 111.4 | 6.545 | 0.281 | 0.154 |
| Fibroblast Cells | 0.133 | 0.0012 | 0.0012 | 20.68 |

Figure 12:
FIG. 12 is a photomicrograph of neocartilage tissue produced using chondrocytes that were maintained under a low attachment condition during expansion.

Gene profile analysis, as measured by quantitative real-time PCR, confirms the hyaline nature of a population of chondrocytes that had been expanded ex vivo using low attachment conditions that maintain chondrocytes in suspension prior to ex vivo growth of neocartilage. The described conditions used to maintain either low or ultra low adherence of chondrocytes to the culture vessel successfully generated progeny that retain the ability to produce tissue engineered neocartilage (FIG. 12). Each of the genes characteristically expressed by articular chondrocytes (Col21A and aggrecan core protein) was expressed to nearly the same level as that of the starting cell population, and in fact was somewhat greater than that of the starting cell population. Importantly, the level of chondrocyte-specific transcription factor (SOX9) measured for each of the neocartilage products showed little change from freshly dissociated chondrocytes harvested from the same donor. Col1A1 gene expression, typically a marker of fibroblastic cells, measured for neocartilage generated from each of the P2 populations of cells showed little change from levels measured for freshly isolated chondrocytes. Moreover, Col1A1 gene expression by chondrocytes contained within neocartilage was measured to be 12% to 16% of that measured for freshly isolated chondrocytes and is clearly distinguishable from fibroblasts. These data provide evidence to support the conclusion that chondrocytes that are subjected to ex vivo expansion under conditions that maintain low or ultra low adherence of the cells to the culture vessel maintain their native phenotype, which translates into retention of chondrocyte morphology and hyaline cartilage gene expression.

EXAMPLE 7

Isolation of Chondrocytes

Unless otherwise indicated, chondrocytes were isolated from the indicated sources by sequential enzymatic digestion as described previously (U.S. Pat. No. 6,235,316). Briefly, minced articular cartilage was exposed to protease from *Streptomyces Griseus* at 37° C. for 20 min., followed by overnight digestion (16-18 hrs) in HL-1 medium (15 mL) containing 2000 units CLS4 collagenase (Worthington, Lakewood, N.J.) and 1200 units hyaluronidase Type VIII (Sigma), Gentamicin (50 µg/mL) and ascorbic acid (50 µg/mL). The next morning, the chondrocyte suspension was gently titrated and pelleted at 500 µg for 8 minutes in a clinical centrifuge.

The harvesting of chondrocytes from expansion culture utilized a reduced concentration of collagenase/hyaluronidase (60/50 units/mL), respectively. Protease from *Streptomyces Griseus* was not necessary for this isolation procedure. Viability and total cell number were estimated using a Guava Personal Cell Analysis System (Guava Technologies, Inc, Hayward, Calif.) and fluorescent detection prior to using the cells in subsequent expansion or differentiation culture. The experiments presented in Example 6 utilized Liberase Enzymes manufactured by Roche Diagnostics Corporation (Indianapolis, Ind.). The concentration of Blendzyme 2 used to isolate chondrocytes from young donor cartilage was established empirically at 6.38 Wunsch units per gram of tissue (5 mL volume). The neutral protease activity of this preparation is 1.4 units thermolysin per gram of tissue. For dissociation of expansion cultures, the final concentration of Blendzyme 2 was 0.2 Wunsch units per mL. Tissue digestion required 8-10 hrs to reach completion, whereas expansion culture digestion was complete at 3-4 hrs.

Cell Culture

Chondrocyte cultures were maintained at 37° C. in a humidified environment supplemented with 5% $CO_2$. Media, as indicated in the examples, included DMEM, both high (HG) and low glucose (LG) formulations, supplemented with 2 mM L-glutamine (Sigma) and 50 µg/mL Gentamicin. HL-1 Complete Serum-free Medium was purchased from Cambrex Bio Science (now Lonzo Walkersville Inc., Walkersville, Md.). HL-1 medium is a chemically defined complete serum-free medium containing less than 30 µg protein/ml. Components of HL-1 include a modified DMEM/F12 base, HEPES buffer, known amounts of insulin, transferrin, sodium selenite and proprietary levels of dihydrotestosterone, ethanolamine, a variety of saturated and unsaturated fatty acids and stabilizing proteins. It contains no bovine serum albumin or other undefined protein mixtures. HL-1 was formulated to support the serum-free growth of various hybridomas and certain other differentiated cells of lymphoid origin.

Chondrocyte expansion cultures were established in HL-1 medium containing gentamicin (50 µg/mL), ascorbic acid (50 µg/mL) and the indicated concentration of recombinant human TGF-β1 or TGF-β3 (10-20 ng/ml) and recombinant human FGF-2 (100 ng/ml). These cytokines were purchased from R&D Systems (Minneapolis, Minn.). A variant form of FGF-2, purchased from ProChon, Ltd (Rehovat, Israel), was used as described in Example 4.

In vitro production of neocartilage for biochemical and gene expression profile analyses was optimized using a proprietary formulation developed at Isto Technologies, Inc. (Media A). This medium was also chemically defined, containing no additional protein source other than 1× insulin, transferrin, selenite mixture available from Sigma (Cat No. I-3146) or recombinant human insulin alone (Serologicals Corporation). Cells were plated at $1 \times 10^6$ per well in 48-well Tissue Culture plates manufactured by Corning (either untreated or treated with HA as indicated). Media exchange occurred twice weekly, and the newly synthesized neocartilage was harvested at day 45, unless otherwise indicated. The rate of proteoglycan synthesis for freshly dissociated chondrocytes derived from young donor cartilage typically was 2 µg S-GAG/µg DNA per day or greater.

Expansion of Chondrocytes in Serum-Containing Medium

Freshly dissociated chondrocytes were seeded in the indicated medium containing ascorbate and Gentamicin at a final density of 0.5 to $3 \times 10^4/cm^2$ using T-75 flasks purchased from Corning. The cultures were maintained for 21 days, with complete exchange of medium occurring twice per week. At culture day 21, chondrocytes were enzymatically dissociated (5-8 hrs) using the collagenase/hyaluronidase mixture described above. Total cell number and viability was estimated using Guava ViaCount® fluorescent cell counting solution and a Guava Personal Cell Analysis system. Guava Viacount® solution distinguishes viable and non-viable cells based on the differential permeability of a combination of DNA-binding dyes in the reagent.

Derivitization of Tissue Culture Polystyrene

The glycosaminoglycan hyaluronic acid was covalently linked to polystyrene culture dishes (6 well plates and 100 mm diameter dishes, Corning) or T75 and T150 flasks, also purchased from Corning, using the procedure defined in Example 2. Briefly, each dish was treated for 2 hr with concentrated sulfuric acid at 37° C., washed extensively with distilled deionized water and then treated with aqueous ammonium hydroxide (30%, v/v) at room temperature for 24 hr. The reactive polysulfonamide (on the plastic surface) was crosslinked to sodium hyaluronate (5 mg/mL; Hylumed Medical, Genzyme; Cambridge, Mass.) using an aqueous solution of 1-ethyl-3(3-dimethylaminopropyl) carbodiimide (25 mg/mL, Sigma). The plates were placed in a humidified atmosphere at 37° C. for 48 hrs. Underivatized HA was removed by aspiration, and the plates were washed extensively with distilled deionized water, followed by two washes with HL-1.

Assessment of Chondrocyte Phenotype-biochemical Analyses

The differentiation potential of expanded chondrocytes was assessed by measuring the total proteoglycan and collagen content of newly synthesized neocartilage matrix. Sulfated glycosaminoglycans, hydroxyproline and deoxyribonucleic acid content were measured using established spectrophotometric methods after papain digestion as described previously. (Farndale and Murray, 1986; Stegemann and Stalder, 1967).

Assessment of Chondrocyte Phenotype-morphological Analyses

Freshly isolated chondrocytes were first expanded on unmodified tissue culture plastic (Example 4 only) in HL-1 Complete Serum-free Medium containing the indicate cytokines, ascorbate and gentamicin. An equal volume of fully supplemented medium was added on day 3, with 50% exchange of medium every 3 to 4 days until harvest. Chondrocytes were dissociated using the collagenase/hyaluronidase mixture described above, and subsequently transferred to 35 mm polystyrene dishes that had been modified via covalent attachment of sodium HA as described above in Derivitization. These cells were expanded to day 10 at which time they were dissociated and viability characterized using Guava ViaCount® reagents as described above. Morphological characterization was performed using a Nikon TMS light microscope outfitted with a Nikon CoolPix995 camera.

Assessment of Chondrocyte Phenotype-Gene Expression Analyses

Neocartilage derived chondrocytes were harvested as indicated for total RNA extraction from disrupted cell pellets using Qbiogene RNApro Solution (Qbiogene Inc, Carlsbad, Calif.), followed by RNeasy Mini Kit (Qiagen Inc, Valencia, Calif.) column purification. Semi-quantitative RT-PCR was performed using 0.5 µg of RNA in a 25 µL reaction mixture with RNA specific primers and the EZ rTth RNA PCR Kit (Perkin Elmer/Applied Biosystems, Foster City, Calif.). All experiments were performed three times on individual donors.

Primers sets used for PCR were selected using the LaserGene PrimerSelect Software, (DNAStar Inc., Madison, Wis.). All PCR primers were designed such that PCR products amplified by a given primer were specific for the gene of interest. The following oligonucleotide primer pairs for human collagen 1A1, 2A1, 9A1, 11A1, aggrecan core protein, N-cadherin, SOX-9, B7-H1 and GAPDH were synthesized at Sigma Genosys (Woodlands, Tex.). Primer pairs are listed in Table VI.

TABLE VI

Primer Pairs Used for Gene Expression Profile Analysis

| Gene | GenBank ID Number | Number of Primer | Sequence of Primer |
|---|---|---|---|
| Aggrecan core | NM_001135 | AGC1-2S | GAAACTTCAGACCATGACAACTC |
| | | AGC1-2AS | ACCAGCAGCACTACCTCCTTC [SEQ ID NO. 1] |

TABLE VI-continued

Primer Pairs Used for Gene Expression Profile Analysis

| Gene | GenBank ID Number | Number of Primer | Sequence of Primer |
|---|---|---|---|
| B7-H1 | NM_014143 | B7-H1-1S<br>B7-H1-1AS | GCTCTTGGTGCTGGCTGGTC<br>TCAGATATACTAGGTGTAGGGAA<br>[SEQ ID NO. 2] |
| B7-1<br>(CD80) | NM_005191 | B7-1-6S<br>B7-1-6AS | GCCATCAACACAACAGTTTCCCAA<br>CAGGGCGTACACTTTCCCTTCTCAA<br>[SEQ ID NO. 3] |
| B7-2<br>(CD86) | NM_006889 | B7-2-6S<br>B7-2-6AS | CTCTCTGGTGCTGCTCCTCTGAA<br>CTGTGGGCTTTTTGTGATGGATGATAC<br>[SEQ ID NO. 4] |
| Col1A1 | NM_000088 | Col1A1-3S<br>Col1A1-3AS | CGAGGGCCAAGACGAAGACA<br>CTTGGTCGGTGGGTGACTCTGA<br>[SEQ ID NO. 5] |
| Col2A1 | NM_033150 | Col2A1-8S<br>Col2A1-8AS | CACCCTGAGTGGAAGAGTGGAGCTAC<br>CAGTGTTGGGAGCCAGATTGTCA<br>[SEQ ID NO. 6] |
| Col19A1 | X54412 | ColA9A1-5S<br>Col9A1-6AS | AAGCACAACTCAGTGCCCCAACAAAAC<br>ATCCCATCACGGCCATCACA<br>[SEQ ID NO. 7] |
| Col11A1 | J04177 | Col11A1-2S<br>Col11A1-2AS | AAGCACAACTCAGTGCCCCAACAAAAC<br>CTACCCGATGCCACTTCCCGTCAG<br>[SEQ ID NO. 8] |
| GAPDH | NM_002046 | GAPDH-1S<br>GAPDH-1AS | GCAAATTCCATGGCACCGTCA<br>CAGGGGTGCTAAGCAGTTGG<br>[SEQ ID NO. 9] |
| N-cadherin | BC036470 | NCAD-1S<br>NCAD-1AS | GGAAAAGTGGCAAGTGGCAGTAAAAT<br>[SEQ ID NO. 10]<br>CCGAGATGGGGTTGATAATGAAGATA<br>[SEQ ID NO. 11] |
| SOX-9 | Z46629 | SOX9-1S<br>SOX9-1AS | GTCAACGGCTCCAGCAAGAACAA<br>[SEQ ID NO. 12]<br>GCTCCGCCTCCTCCACGAA<br>[SEQ ID NO. 13] |

Semi-quantitative RT-PCR was performed using 0.5 μg of total RNA with 1 μl *Thermus Thermophilus* Polymerase (2.5 U/μl), 0.75 μL of each 10 mM dNTP, 5 μL of 5xEZ RT-PCR Buffer, 2.5 μL of 25 mM Mn(OAc)$_2$, and 2 μL of 5 μM stocks (0.4 μM final conc.) of upstream and downstream primers in a total volume of 25 μl. The final concentration of Mn(OAc)$_2$ in the buffer was 2.5 mM. The solutions were denatured at 94° C. for 1 minute prior to RT-PCR amplification using a programmable thermocycler (I-cycler, Bio-Rad Labs Inc., Hercules, Calif.) under the following conditions: Denaturation, 94° C. for 1 min., reverse transcriptase reaction at 58° C. for 30 min., followed by denaturation at 94° C. for 1 min., then PCR Cycling with 94° C. denaturation for 45 sec., and annealing and extension at 58° C. for 1 min. 10 seconds, for a total of 42 cycles. A final extension at 58° C. for 8 min. was performed, and the reaction products were stored at −80° C. PCR products were separated by electrophoresis on 2.5% agarose gels containing ethidium bromide. Gels were run at 80 V for approximately 90 min and photographed under UV light. Each experiment was performed a minimum of three times to confirm reproducibility.

Statistics

Prism software (version 3.0), manufactured by Graph Pad Software (San Diego, Calif.), was used to create graphic data. Data are presented as the mean+/−SD with replicates of three (3) to five (5). Significance between groups was determined using the statistical package within the Prism suite.

EXAMPLE 8

Adult Chondrocytes Expanded on Hyaluronate Modified Substrates Show Enhanced Matrix Formation Potential This example demonstrates that adult chondrocytes expanded on an HA-modified substrate in chemically defined serum-free medium significantly increased matrix formation of the expanded cells by greater than four-fold.

Chondrocytes derived from the articular cartilage of a 47 year-old male were expanded in HL-1 Complete Serum-free medium containing 100 ng/mL FGF-2 and 20 ng/mL TGF-β1, 50 μg/mL Gentamicin and 50 μg/mL ascorbic acid. Two million cells were seeded into 100 mm diameter plates that had been modified by covalent attachment of sodium hyaluronate. Expansion cultures were maintained for a total of 17 days as described above (at each passage). Chondrocytes were subsequently released from the culture surface using a combination of collagenase/hyaluronidase, washed in HL-1 medium and total cell number and viability were measured using Guava Viacount® reagents.

Figure 13:
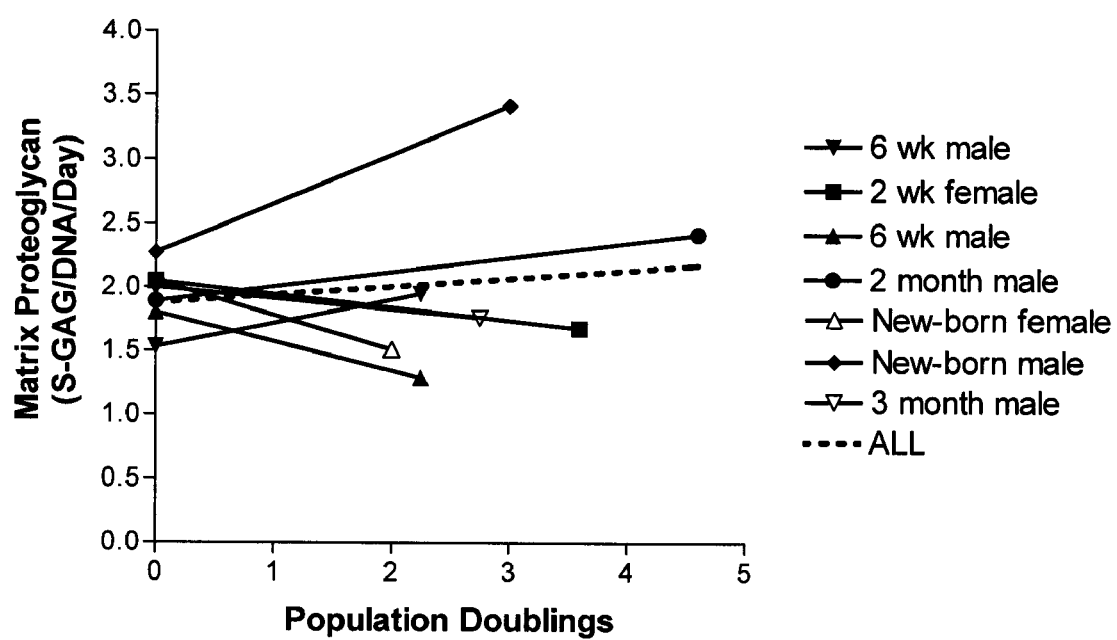
FIG. 13 is a graphic representation showing the biochemical composition of neocartilage tissue grafts that were produced from adult chondrocytes that were expanded on HA-modified polystyrene through two passages in a chemically defined serum-free medium containing bFGF, TGF-β and vitamin C through a cumulative increase of 5.8 population doublings.

A portion of the first passage cells were placed into differentiation (tissue production) culture as described above to measure matrix formation potential for comparison with neocartilage produced from primary cells (FIG. 11). Two additional 100 mm diameter plates were set up (2 million cells per plate) for serial expansion to passage two, and the matrix formation potential of these expanded cells was assayed using the same method. Under these conditions, passage one and two cells demonstrated 3 and 2.7 population doublings, respectively, resulting in a cumulative increase of nearly 64-fold at day 34 of culture. The biochemical composition of newly synthesized neocartilage matrix produced (at day 45) from both the freshly isolated and expanded cells is shown in FIG. 13. Chondrocytes were isolated from a 47-year-old male displaying Grade 1 osteoarthritis. Differentiation (tissue production) medium containing Vitamin C (Medium A) further contained either dexamethasone ($10^{-8}$ M; Sigma) or a combination of dexamethasone and FGF-2 (10 ng/mL) as indicated to further induce proteoglycan synthesis relative to the primary cells maintained in Medium A containing Vitamin C alone. The standard assay compared matrix formation in Medium A containing vitamin C, with the two additional groups of cells (primary culture alone) that were grown in Medium A further supplemented with dexamethasone 21-phosphate ($10^{-8}$ M; Sigma) or the combination of dexamethasone and FGF-2 (10 ng/mL). (Dexa, dexamethasone 21-phosphate; bFGF, recombinant human fibroblast basic growth factor-2; * denotes significance (P<0.05)).

Each population of expanded cells produced neocartilage that contained four-fold greater levels of sulfated glycosaminoglycans than the freshly isolated cells derived from the same donor (FIG. 13). The level of proteoglycan synthesis in the expanded cells was indistinguishable from that of primary cells that had been maintained in Media A containing dexamethasone alone or the combination of basic FGF and dexamethasone. These data show that expansion of adult chondrocytes on HA-modified substrates maintains the full differentiation potential of adult chondrocytes.

Alternative embodiments of the method include certain modifications in the tissue culture process during expansion and extracellular matrix production, which have been found to facilitate phenotype retention by the expanded population of chondrocytes. The alternative embodiments described herein all share at least one initial expansion phase followed by a period of extracellular matrix production and harvesting of the final tissue product. One or more periods of expansion are involved, and cryopreservation steps may also be incorporated. For example, a first expansion phase is optionally followed by a period of cryopreservation after which the population of cells having undergone the first expansion are thawed and returned to expansion conditions for a second phase of expansion. An expanded population of cells having undergone two phases of expansion optionally undergoes a second period of cryopreservation, or is seeded onto a tissue culture substrate under appropriate conditions for tissue growth and extracellular matrix production to produce neocartilage. In another embodiment, the expanded population of cells is ready for transplant into a subject for tissue repair. In an illustrative embodiment, the expanded population of cells is maintained for a period under cryopreservation and later retrieved for transplant. The expanded population is well-suited for transplant by injection, for example by directly injecting the expanded population of cells into a joint of a subject in need of cartilage repair. In other words, the expanded population of cells is suitable for transplantation into a subject without the requirement of a subsequent period of cell culture for ECM production.

As with the method described elsewhere herein, the chondrocytes are selected from cartilaginous tissue that is isolated from either juveniles or adults, such as but not limited to articular cartilage. Other suitable sources of chondroprogenitor cells include, without limitation, mesenchymal stem cells, cartilage cells, umbilical cord stem cells, bone marrow stromal cells, adipose stromal cells or chondrogenic progenitor cells derived from periosteum or synovium, and also transgenic chondrocytes resistant to immune-mediated xenograft rejection.

As described herein, an initial chondrocyte expansion phase lasting at least about fourteen (14) days up to twenty-one (21) days is performed under low attachment conditions that limit or prevent chondrocyte attachment to the tissue culture substrate. This is accomplished, for example, by using an HA-modified substrate as described elsewhere herein, use of an unmodified substrate in the presence of an expansion medium containing HA in solution, or use of other substrates to which a coating of a commercially available low attachment material has been applied. In another embodiment, the method contemplates use of an unmodified substrate in the presence of an expansion medium containing another low-attachment additive other than HA in solution, such as the soybean lecithin phosphatidyl choline. With regard to substrates, a low attachment substrate is any substrate comprised of a suitable material, or to which a surface coating has been applied, such that a majority of isolated cells seeded onto the substrate do not attach to the substrate. Such low attachment substrates, like other low attachment conditions described herein, have been shown to result in colony formation (clusters) by chondrocytes undergoing expansion, as well as phenotype retention. For coated substrates, suitable low attachment coatings include any coating material such as those described herein and elsewhere that limits chondrocyte attachment during the expansion of the initial population of chondrocytes, and thereby limits or prevents dedifferentiation and so results in phenotype retention by the chondrocytes. Conditions of low cell attachment encompass conditions established using commercially available products and materials sometimes referred to in the literature and elsewhere as "ultra low cell attachment" and "ULA", such as, for example, products having the "Ultra-Low Attachment" surface from Corning, Inc. (Acton, Mass., USA), comparable products also with surface coatings from Nalge Nunc International (Rochester, N.Y.) and products available from Cell-Seed (Japan).

In addition, a serum-free expansion medium (SFM, Gibco) is used for bathing the cells. TGF-β, FGF, L-glutamine and Vitamin C are added to the SFM at concentrations in solution of 10 ng/ml, 100 ng/ml, 4 mM and 50 μg/ml respectively. The supplemented SFM is either replaced or further supplemented with TGF-β, FGF, L-glutamine and Vitamin C at regular three to four day intervals to maintain the final concentrations in solution for each as set forth above.

At approximately culture day 21, the expanded cells are harvested by enzymatic dissociation using a purified collagenase, for example Liberase™ Blendzyme 2 available from Roche Diagnostics Corporation, Roche Applied Science (Indianapolis, Ind., USA), and placed into cryopreservation. With this expansion approach, as with the methods described elsewhere herein, phenotype retention is demonstrated by observation of a rounded, not spread morphology and low expression of Type I collagen as determined by measurement of mRNA levels. Specifically, after at least 3.8 doublings of the chondrocyte population, at least 50% of the chondrocytes retain rounded morphology and hyaline cartilage gene expression. With currently available methods the expansion can be maintained through as many as 8 to 10 doublings before a substantial portion of the cells demonstrate loss of phenotype. However, it will be recognized that with ongoing discovery and development of other growth factors and availability of improved materials and methods, cells may be expanded through more than 8 to 10 doublings while at least 50% of cells retain phenotype as determined by cell morphology and hyaline cartilage gene expression as described elsewhere herein.

For cryopreservation, the harvested expanded chondrocyte population is suspended in a suitable commercially available cryoprotectant such as Cryostor™ to produce a cell suspension having a density of no more than about $1.7 \times 10^8$ cells per milliliter of suspension. After a suitable incubation time, one-milliliter aliquots of the cell suspension are delivered to cryovials so that each cryovial contains as many as $1.7 \times 10^8$ cells. The cryovials are frozen and placed in cryostorage at $-150°$ C. for later retrieval, thaw and transplantation by injection, or extracellular matrix production or for a second round of expansion by repeating the same expansion steps using low attachment conditions and SFM supplemented as noted above with TGF-β, FGF, L-glutamine and Vitamin C in concentrations as set forth above. For example, an exemplary embodiment of the method includes a primary cell expansion followed by a first period of cryopreservation, then a secondary cell expansion and finally a second period of cryopreservation before the process of extracellular matrix production is started. However, it is recognized that during commercial-scale manufacturing, the intermediate hold-step (cryopreservation) at passage 1 is optionally eliminated.

In an illustrative embodiment, the initial expansion and cryopreservation phases, whether one round or two of each, are followed by extracellular matrix production in a transwell apparatus as described herein. The transwell apparatus was developed to solve the problem presented by the diffusion barriers created when a typical tissue culture substrate is used. In particular, the extracellular matrix itself creates a diffusion barrier as tissue is grown from an initial population of chondrocytes and the extracellular matrix is deposited around the cells. The extracellular matrix is a diffusion barrier to molecules moving into and out of the cells which are critical to cells' survival and growth. In addition, the typically used impermeable tissue culture substrate magnifies the diffusion problem by creating a barrier to diffusion over about half of the cellular surface area, i.e. the cell surfaces that contact the substrate. Described herein is a novel approach to culturing the chondrocytes that minimizes the diffusion barrier problem. The inventors have found success in culturing chondrocytes in a bathing solution of suitable tissue production medium on a permeable, uncoated polycarbonate membrane having multiple pores therethrough. For matrix production, any commonly commercially available polycarbonate substrate without any surface modification has been found to perform remarkably well as a chondroconductive substrate.

In one embodiment, the polycarbonate substrate is a membrane having a thickness of 10 microns. The pores of the polycarbonate tissue culture substrate are characterized by an inner diameter of at least about 1 micron to about 12 microns. In an exemplary embodiment, the population of pores is characterized by inner diameters having a normal distribution centered around 3 microns, with hardly any or no pores having inner diameters of less than 1 micron. Pore density across the surface of the substrate is about $2 \times 10^6 / cm^2$. Unexpectedly, and in contrast to teachings elsewhere (e.g. U.S. Pat. No. 5,326,357), use of a substrate with pores of an inner diameter of less than about 1 micron has been observed to be insufficient to surmount the diffusion barrier problem presented by an otherwise impermeable substrate and can result in cell death. The difference in results among investigators may relate to procedural differences in the type (the material and pore density or total pore area) and treatment of the porous substrates used. Alternatively, and without being bound to a particular theory, a pore size of greater than 1 micron may be required to meet the diffusion requirements of juvenile chondrocytes. Juvenile chondrocytes have been shown to produce extracellular matrix at a significantly greater rate than that of adult chondrocytes. In either case, the inventors have succeeded in demonstrating that a population of chondrocytes expanded according to the methods as described herein and then maintained in tissue production medium on a perforated substrate of polycarbonate with pores having an inner diameter of at least about 1 micron, at currently commercially available pore densities, are observed to both retain phenotype and to demonstrate random cellular organization under microscopic examination, as described in further detail, for example, in U.S. Pat. No. 6,235,316. The random cellular organization stands in contrast to other methods that produce stratified tissue having distinct superficial, mid- and deep regions as determined under microscopic examination. (e.g. U.S. Pat. No. 5,326,357).

In an exemplary embodiment, the permeable polycarbonate substrate is used in a transwell configuration for extracellular matrix production. A substrate is placed within a well of a multiwell plate, for example a six well plate, and cells from the expanded population of chondrocytes are seeded onto the substrate within the well. Cells are seeded, for example, at a density of about $1 \times 10^6$ cells/cm$^2$. Extracellular matrix production takes place during a predetermined serum-free culture period of at least about 45 days, typically lasting 60-65 days, after which the cultured tissue is ready for harvest, packaging and ultimately implantation. For the first seven days of the extracellular matrix production period, cells are maintained in the transwell plates under conditions appropriate to minimize exposure to contaminants. A suitable chemically defined tissue production medium is supplied to the wells and refreshed regularly by manual delivery or using an automated equivalent method. During this initial seven day period, the tissue production medium optionally includes an amount of TGF-β in solution, preferably at a concentration of about 10 ng/ml of solution.

After the initial seven days of extracellular matrix production, the cells in culture on the permeable polycarbonate substrate, and in process of producing extracellular matrix, are transferred together with the substrate to a polystyrene or similar culture well of a predetermined shape and selected dimensions. Multiple culture wells each containing cells seeded onto the permeable polycarbonate substrate, are then maintained in a serum-free tissue production medium without added TGF-β, at a controlled temperature (37° C.) and atmosphere (10% $CO_2$ in air) during the remainder of the predetermined culture period of at least 45 days.

The shape and dimensions of the cartilaginous tissue implants (neocartilage) resulting after the period of extracellular matrix production are determined by the shape and dimensions of the culture well inasmuch as side walls of the well constrain the outgrowth of the tissue by forming a barrier to cell migration. The culture well can be fabricated from a suitable material such as polystyrene, or can be fabricated from other materials that form a migration barrier to the cells while still allowing certain nutrients such as gases and cell supplements in solution to pass through the barrier. The material forming the side walls of the well can be selected for the ability to allow selected cell nutrients to pass through while preventing other unhelpful or perhaps damaging molecules from passing through. Moreover, the culture well can be configured in a variety of different shapes and sizes as determined by the intended geometrical characteristics of the cultured tissue product and implant needs.

Referring to FIG. 10, the three panels FIGS. 10A, 10B and 10C are each, respectively, a photomicrograph of cells expanded under one of three low cell attachment conditions: using an HA-modified polystyrene substrate (FIG. 10A), using an unmodified polystyrene substrate in combination with HA in solution in the expansion medium (FIG. 10B), chondrocyte appearance and cluster formation (arrows) was observed for each of the three low attachment expansion conditions used, each of which controlled cell attachment and spreading during expansion.

FIG. 12 is a photomicrograph illustrating the histological appearance of neocartilage produced from chondrocytes that were expanded through three (3) to four (4) population doublings under a low attachment condition. The expanded population was then transferred to a perforated polycarbonate membrane characterized by pores having an inner diameter of 3 microns. The photomicrograph shows that the chondrocytes have produced an extensive extracellular matrix and further that the cells are randomly organized within the newly synthesized matrix.

OTHER EMBODIMENTS

As various changes could be made in the above constructions without departing from the scope of the invention, it is intended that all matter contained in the above description or shown in the accompanying drawings shall be interpreted as illustrative and not in a limiting sense. Indeed, various modifications of the invention in addition to those shown and described herein will become apparent to those skilled in the art from the foregoing description which does not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

REFERENCES CITED

| U.S. Patent Documents | | | |
|---|---|---|---|
| 6235316B1 | May 22, 2001 | Adkisson | 424/548 |
| 6582960 | Jun. 24, 2003 | Martin et al. | 435/377 |
| 6617161 | Sep. 9, 2003 | Luyten et al. | 435/375 |
| 6645764B1 | Nov. 11, 2003 | Adkisson | 435/375 |
| 5830741 | Nov. 3, 1998 | Dwulet et al. | 435/220 |
| 5716404 | Feb. 10, 1998 | Vacanti et al. | 623/8 |
| 5753485 | May 19, 1998 | Dwulet et al. | 435/220 |
| 4356261 | Oct. 26, 1982 | Kuettner | 435/68 |
| 2003/0215426A1 | Nov. 20, 2003 | French et al. | 424/93.7 |

OTHER REFERENCES

Adkisson et al., "In vitro generation of scaffold independent neocartilage", Clin. Orthop., 391S, pp. S280-S294 (2001).

Benya and Shaffer, "Dedifferentiated Chondrocytes Reexpress the Differentiated Collagen Phenotype when Cultured in Agarose Gels", Cell, vol. 30, pp. 215-224 (1982).

Dell'Accio et al., "Molecular markers predictive of the capacity of expanded human articular chondrocytes to form stable cartilage in vivo", Arthritis & Rheumatism, vol. 44, pp. (2001).

Farndale and Murray, "Improved quantization and discrimination of sulphated glycosaminoglycans by use of dimethylmethylene blue" Biochem. Biophys. Acta., vol. 883, pp. 173-177 (986).

Hauselmann et al., "Phenotypic stability of bovine articular chondrocytes after long-term culture in alginate beads", J. Cell Science, vol. 107, pp. 17-27 (1994).

Hauselmann et al., "Adult human chondrocytes cultured in alginate form a matrix similar to native human articular cartilage", Am. J. Physiol., vol. 271, pp. C742-C752 (1996).

Homicz et al., "Effects of serial expansion of septal chondrocytes on tissue engineered neocartilage production", Otolaryngol. Head Neck Surg., vol. 127, pp. 398-408

Huang et al., "Chondrogenic potential of multipotential cells from human adipose tissue", Plastic and Reconstructive Surgery, vol. 113, pp. 585-594 (2004).

Hunziker, "Articular cartilage repair: Basic science and clinical progress. A review of the current status and prospects", OsteoArthritis and Cartilage, vol. 10, pp. 432-463 (2002).

Jakob et al., "Specific growth factors during the expansion and redifferentiation of adult human articular chondrocytes enhance chondrogenesis and cartilaginous tissue formation in vitro", J. Cell. Biol., vol. 81, pp. 368-377 (2001).

Kavalkovick et al., "Chondrogenic differentiation of human mesenchymal stem cells within an alginate layer culture system", In Vitro Cell. Dev. Biol. Animal, vol. 38, pp. 457-466 (2002).

Kogler et al., "A new human somatic stem cell from placental cord blood with intrinsic pluripotent differentiation potential", J. Exp. Med., vol. 200, pp. 123-135 (2004).

Kujawa et al, "Hyaluronic acid bonded to cell-culture surfaces stimulates chondrogenesis in stage 24 limb mesenchyme cell cultures", Dev. Bio., vol. 114, pp. 504-18 (1986).

Kujawa et al., "Substrate-bonded hyaluronic acid exhibits a size-dependent stimulation of chondrogenic differentiation of stage 24 limb mesenchymal cells in culture", Dev. Bio., vol. 114, pp. 519-28 (1986).

Kujawa et al., "Hyaluronic acid bonded to cell culture surfaces inhibits the program of myogenesis", Dev. Bio., vol. 113, pp. 10-16 (1986).

Laurent, "Structure of hyaluronic acid. In: the chemistry and molecular biology of the intercellular matrix, (Balazs ed.), vol. 2, pp. 703-732, Academic Press, New York (1970).

Laurent and Fraser, "Hyaluronan", FASEB J., vol. 6, pp. 2397-2404 (1992).

Liu et al., "An osteoconductive collagen/hyaluronate matrix for bone regeneration", Biomaterials, vol. 20, pp. 1097-1108.

Mackay et al., "Chondrogenic differentiation of cultured human mesenchymal stem cells from marrow" Tissue Eng., vol. 4, pp. 415-428 (1998).

Malpeli et al., "Serum-free growth medium sustains commitment of human articular chondrocyte through maintenance of Sox9 expression", Tiss. Eng., vol. 10, pp. 145-155 (2004).

Mandl et al., "Serum-free medium supplemented with high concentrations of FGF-2 for cell expansion culture of human ear chondrocytes promotes redifferentiation capacity" Tiss. Eng., vol. 4, pp. 573-580 (2002).

Mandl et al., "Multiplication of human chondrocytes with low seeing densities accelerates cell yield without losing redifferentiation capacity", Tiss. Eng., vol. 10, pp. 109-118 (2004).

Ornitz and Itoh, "Fibroblast growth factors", Genome Biol., vol. 2 (3), pp. 3005.1-3005.12 (2001).

Ornitz, "FGFs, heparan sulfate and FGFRs: complex interactions essential for development", BioEssays, vol. 22, pp. 108-112 (2000).

Osman et al., "Combined transgenic expression of {acute over (.alpha.)}-galactosidase and 1,2-fucosyltransferase leads to optimal reduction in the major xenoepitope Gal{acute over (.alpha.)}/(1,3) Gal", Proc. Natl. Acad. Sci., vol. 94, pp. 14677-14682 (1997).

Plotnikov et al., "Crystal structures of two FGF-FGFR complexes reveal the determinants of ligand-receptor specificity", Cell, vol. 101, pp. 413-424 (2000).

Reginato et al., "Formation of nodular structures resembling mature articular cartilage in long-term primary cultures of human fetal epiphyseal chondrocytes on a hydrogel substrate", Arthritis & Rheumatism, vol. 37, pp. 1338-1349 (1994).

Sandrin et al., "Enzymatic remodeling of the carbohydrate surface of a xenogenic cell substantially reduces human antibody binding and complement-mediated cytolysis", Nature Med., vol. 1, pp. 1261-1267 (1995).

Sekiya et al., "Dexamethasone enhances SOX9 expression in chondrocytes", J. Endocrinol., vol. 169, pp. 573-579 (2001).

Singley and Solursh, "The spatial distribution of hyaluronic acid and mesenchymal condensation in the embryonic chick wing", Dev. Biol., vol. 84, pp. 102-120 (1981).

Stegmann and Stalder, "Determination of hydroxyproline", Clin. Chim. Acta, vol. 18, pp. 267-273 (1967).

Turley and Roth, "Spontaneous glycosylation of glycosaminoglycan substrates by adherent fibroblasts", Cell, vol. 17, pp. 109-115 (1979).

Vacanti, "Beyond Transplantation", Arch. Surg., vol. 123, pp. 545-549 (1998).

Vacanti et al., "Selective cell transplantation using bioabsorbable artificial polymers as matrices", J. Pediatr. Surg., vol. 23, pp. 3-9 (1998).

West et al., "Angiogenesis induced by degradation products of hyaluronic acid", Science vol. 228, pp. 1324-1326 (1985).

Yoon et al., "Maintenance of differentiated phenotype of articular chondrocytes by protein kinase C and extracellular signal-regulated protein kinase", Biochem. J., vol. 277, pp. 8412-8420 (2002).

22 1 23 DNA Artificial AGC1-2S primer, Aggrecan core, GenBank ID No. NM_01135 1 gaaacttcag accatgacaa ctc 23 2 21 DNA Artificial AGC1-2AS primer, Aggrecan core, GenBank ID No. NM_01135 2 accagcagca ctacctcctt c 21 3 20 DNA Artificial B7-H1-1S primer, B7-H1, GenBank ID No. NM_014143 3 gctcttggtg ctggctggtc 20 4 23 DNA Artificial B7-H1-1AS primer, B7-H1, GenBank ID No. NM_014143 4 tcagatatac taggtgtagg gaa 23 5 24 DNA Artificial B7-1-6S primer, B7-1, GenBank ID No. NM_005191 5 gccatcaaca caacagtttc ccaa 24 6 25 DNA Artificial B7-1-6AS primer, B7-1 (CD80), GenBank ID No. NM_005191 6 cagggcgtac actttccctt ctcaa 25 7 23 DNA Artificial B7-2-6S primer, B7-2, GenBank ID No. NM_006889 7 ctctctggtg ctgctcctct gaa 23 8 27 DNA Artificial B7-1-6AS primer, B7-2 (CD86), GenBank ID No. NM_006889 8 ctgtgggctt tttgtgatgg atgatac 27 9 20 DNA Artificial Col1A1-3S primer, Col1A1, GenBank ID No. NM_000088 9 cgagggccaa gacgaagaca 20 10 22 DNA Artificial Col1A1-3AS primer, Col1A1, GenBank ID No. NM_000088 10 cttggtcggt gggtgactct ga 22 11 26 DNA Artificial Col2A1-8S primer, Col2A1, GenBank ID No. NM_033150 11 caccctgagt ggaagagtgg agctac 26 12 23 DNA Artificial Col2A1-8AS primer, Col2A1, GenBank ID No. NM_033150 12 cagtgttggg agccagattg tca 23 13 27 DNA Artificial Col9A1-5S primer, Col9A1, GenBank ID No. X54412 13 aagcacaact cagtgcccca acaaaac 27 14 20 DNA Artificial Col9A1-6AS primer, Col9A1, GenBank ID No. X54412 14 atcccatcac ggccatcaca 20 15 27 DNA Artificial Col11A1-2S primer, Col11A1, GenBank ID No. J04177 15 aagcacaact cagtgcccca acaaaac 27 16 24 DNA Artificial Col11A1-2AS primer, Col11A1, GenBank ID No. J04177 16 ctacccgatg ccacttcccg tcag 24 17 21 DNA Artificial GAPDH-LS primer, GAPDH, GenBank ID No. NM_002046 17 gcaaattcca tggcaccgtc a 21 18 20 DNA Artificial GAPDH-1AS primer, GAPDH, GenBank ID No. NM_002046 18 caggggtgct aagcagttgg 20 19 26 DNA Artificial NCAD-1S primer, N-cadherin, GenBank ID No. BC036470 19 ggaaaagtgg caagtggcag taaaat 26 20 26 DNA Artificial NCAD-1AS primer, N-cadherin, GenBank ID No. BC036470 20 ccgagatggg gttgataatg aagata 26 21 23 DNA Artificial SOX9-1S primer, SOX-9, GenBank ID No. Z46629 21 gtcaacggct ccagcaagaa caa 23 22 19 DNA Artificial SOX9-1AS primer, SOX-9, GenBank ID No. Z46629 22 gctccgcctc ctccacgaa 19

---

We claim:

1. An in vitro method for producing cartilage tissue characterized by a random organization of cells, the method comprising:
  (a) isolating a population of chondrocytes from donor cartilage tissue; then
  (b) expanding the population of cartilage chondrocytes in an expansion medium on a substrate comprising polystyrene and hyaluronic acid covalently bound to each other to yield expanded chondrocytes, wherein the expansion conditions are effective to prevent attachment of a majority of the chondrocytes to the substrate; then
  (c) seeding a plurality of expanded chondrocytes in a tissue production medium on a porous polycarbonate substrate having a plurality of pores therethrough, the pores having an inner diameter between about 1 micron and about 12 microns; and then
  (d) culturing the expanded chondrocytes on the porous polycarbonate substrate for a period of time sufficient for the chondrocytes to produce extracellular matrix,
  thereby producing in vitro a cultured cartilage tissue characterized by a random organization of cells.

2. A method according to claim 1 wherein expanding under conditions effective to prevent attachment of a majority of the chondrocytes to the substrate during expansion comprises use of a substrate having a coating that reduces cell attachment to the substrate relative to cell attachment to an uncoated substrate.

3. A method according to claim 1 wherein the expansion medium is a serum-free medium.

4. A method according to claim 1 wherein the tissue production medium comprises TGF-β.

5. A method according to claim 1 wherein the population of chondrocytes comprises synovial capsule chondrocytes or periosteum chondrocytes.

6. A method according to claim 1 wherein the population of chondrocytes comprises juvenile articular chondrocytes.

7. A method according to claim 1 wherein the population of chondrocytes comprises adult articular chondrocytes.

8. A method according to claim 1 comprising adding TGF-β to the tissue production medium in an amount of 10 ng/ml of the medium.

9. A method according to claim 1, wherein expanding the population of chondrocytes comprises:
  a first phase of cell expansion; and
  a second phase of cell expansion following the first phase of cell expansion.

10. A method according to claim 9 further comprising maintaining the population of chondrocytes for a culture period of about forty-five (45) to about sixty-five (65) days in the tissue production medium.

11. A method according to claim 9 wherein maintaining the population of chondrocytes in a tissue production medium comprises maintaining a predetermined level of oxygen and carbon dioxide in the tissue production medium.

12. A method according to claim 1 wherein the polycarbonate substrate comprises a polycarbonate membrane, wherein the pores comprise perforations through the membrane.

13. A method according to claim 1 wherein the donor cartilage tissue comprises immature hyaline cartilage tissue and the chondrocytes comprise immature hyaline cartilage chondrocytes.

14. A method according to claim 13 wherein the conditions during expansion are further effective for the population of chondrocytes to undergo at least 3.8 doublings of the chondrocyte population while at least 50% of the chondrocytes retain rounded morphology and hyaline cartilage gene expression.

15. A method according to claim 1 wherein the step of expanding the population of chondrocytes under conditions that reduce chondrocyte attachment to the substrate during expansion comprises use of soluble hyaluronic acid in the expansion medium.

* * * * *

UNITED STATES PATENT AND TRADEMARK OFFICE
CERTIFICATE OF CORRECTION

| | | |
|---|---|---|
| PATENT NO. | : 8,017,394 B2 | Page 1 of 1 |
| APPLICATION NO. | : 11/859524 | |
| DATED | : September 13, 2011 | |
| INVENTOR(S) | : H. Davis Adkisson, IV et al. | |

It is certified that error appears in the above-identified patent and that said Letters Patent is hereby corrected as shown below:

IN THE CLAIMS:

Col. 50, Claim 10, line 1: "according to claim 9" should read --according to claim 1--

Signed and Sealed this
Twenty-seventh Day of March, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,017,394 B2 | Page 1 of 1 |
| APPLICATION NO. | : 11/859524 | |
| DATED | : September 13, 2011 | |
| INVENTOR(S) | : H. Davis Adkisson, IV et al. | |

It is certified that error appears in the above-identified patent and that said Letters Patent is hereby corrected as shown below:

IN THE CLAIMS:

Column 50, line 23 (Claim 10, line 1) "according to claim 9" should read --according to claim 1--

This certificate supersedes the Certificate of Correction issued March 27, 2012.

Signed and Sealed this
Seventeenth Day of April, 2012

David J. Kappos
*Director of the United States Patent and Trademark Office*